United States Patent [19]

Otera et al.

[11] Patent Number: 4,876,400
[45] Date of Patent: Oct. 24, 1989

[54] PROCESS FOR PRODUCING VITAMIN A OR ITS CARBOXYLIC ACID ESTERS, AND ITERMEDIATE COMPOUNDS USEFUL FOR THE PROCESS

[75] Inventors: Junzo Otera, Okayama City, Japan; Tadakatsu Mandai, Ithaca, N.Y.; Mikio Kawada, Okayama City, Japan

[73] Assignee: Kuraray Co., Ltd., Kurashiki, Japan

[21] Appl. No.: 215,167

[22] Filed: Jul. 5, 1988

Related U.S. Application Data

[62] Division of Ser. No. 804,252, Dec. 3, 1985, Pat. No. 4,825,006.

[30] Foreign Application Priority Data

| Jan. 10, 1985 | [JP] | Japan | 60-2964 |
| Mar. 1, 1985 | [JP] | Japan | 60-41667 |
| Oct. 11, 1985 | [JP] | Japan | 60-227549 |
| Oct. 11, 1985 | [JP] | Japan | 60-227550 |
| Oct. 16, 1985 | [JP] | Japan | 60-232073 |
| Oct. 16, 1985 | [JP] | Japan | 60-232074 |

[51] Int. Cl.$^4$ .............................. C07C 35/18
[52] U.S. Cl. .................................. 568/824
[58] Field of Search ............... 560/255, 260; 568/32, 568/832; 549/420

[56] References Cited

U.S. PATENT DOCUMENTS

| 3,848,000 | 11/1974 | Chabardes et al. | 568/32 |
| 3,979,471 | 11/1976 | Julia | 568/32 |
| 4,175,205 | 11/1979 | Decor | 568/32 |

FOREIGN PATENT DOCUMENTS

631533 11/1949 United Kingdom ............... 560/260

OTHER PUBLICATIONS

Mandai et al., "Novel Synthesis of Acteylenes and Polyenes via Desulfonylation reaction", J. Amer. Chem. Soc.—vol. 106 (1984), pp. 3670-3672.

*Primary Examiner*—Werren B. Lone
*Attorney, Agent, or Firm*—Wenderoth, Lind & Ponack

[57] ABSTRACT

A process for producing vitamin A represented by the formula

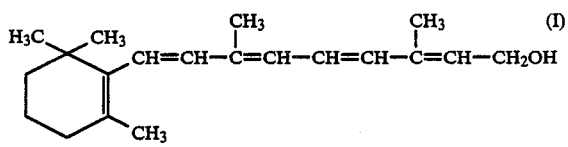

which comprises treating a compound represented by the formula

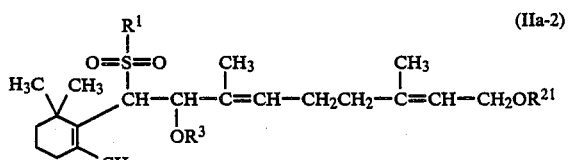

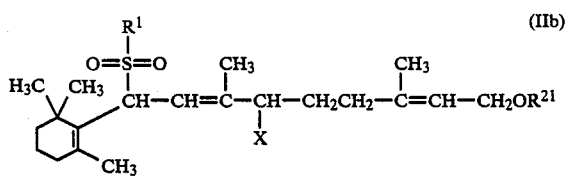

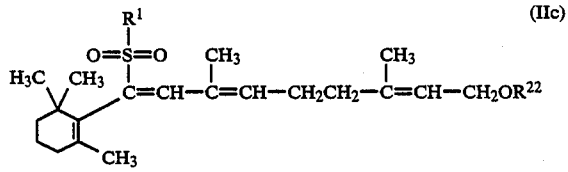

wherein $R^1$ represents an aryl group which may be substituted, $R^{21}$ and $R^{22}$ each represent a hydrogen atom or a lower alkanoyl group, $R^3$ represents an acetal-type protective group for a hydroxyl group, and X represents a halogen atom, with a base; and novel intermediate compounds useful for the above process.

8 Claims, No Drawings

PROCESS FOR PRODUCING VITAMIN A OR ITS CARBOXYLIC ACID ESTERS, AND ITERMEDIATE COMPOUNDS USEFUL FOR THE PROCESS

This is a Rule 60 Divisional application of Ser. No. 804,252, filed Feb. 3, 1988, now U.S. Pat. No. 4,825,006.

This invention relates to a process for producing vitamin A or its carboxylic acid ester and to novel intermediate compounds useful for the process.

Vitamin A and its carboxylic acid esters typified by the acetate and palmitate are used in great quantities as medicines, feed additives, etc. The following methods have previously been proposed for the production of vitamin A and its carboxylates.

(1) Helvetica Chimica Acta, 30, 1911 (1947)

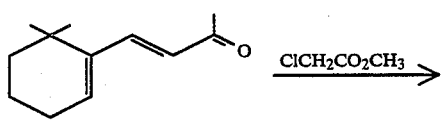

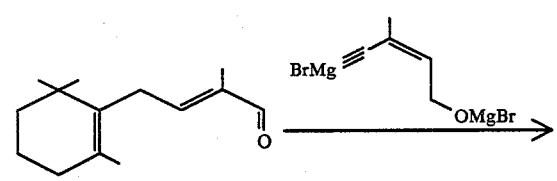

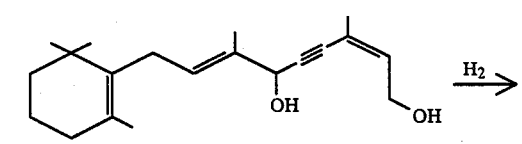

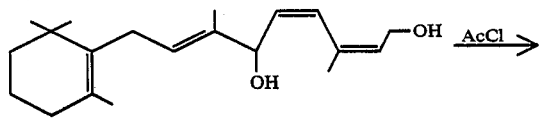

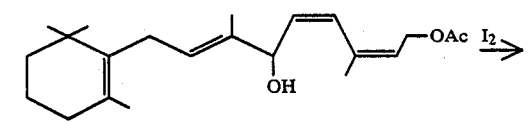

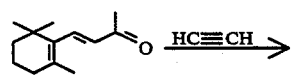

(wherein Ac=acetyl group)

(2) Chemie Ingeniuor Techik, 45, 646 (1973)

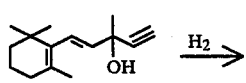

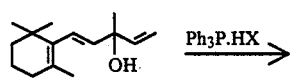

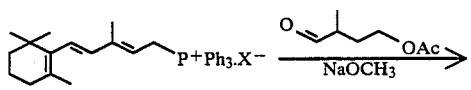

Vitamin A acetate $\xrightarrow{\text{hydrolysis}}$ Vitamin A (wherein Ph=phenyl group, X=halogen atom, Ac=acetyl group)

(3) Helvetica Chimica Acta, 59, Fasc. 2, 387 (1976)

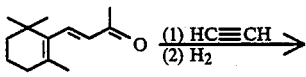

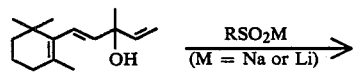

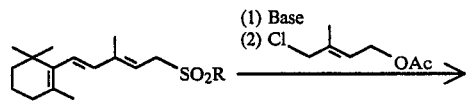

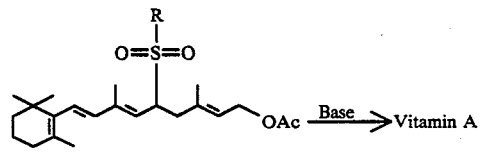

(wherein Ac=acetyl group)

(4) J. Org. Chem., 41, 3287 (1976)

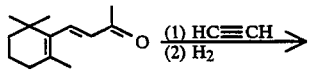

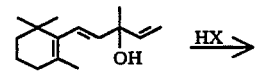

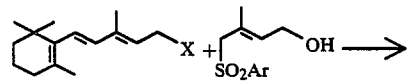

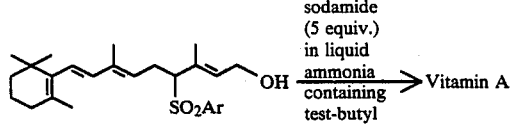

Very recently, the present inventors and their co-workers proposed the following method for the production of vitamin A acid methyl ester.

(5) J. Am. Chem. Soc., 106, 3670 (1984)

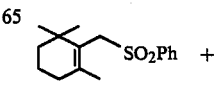

-continued

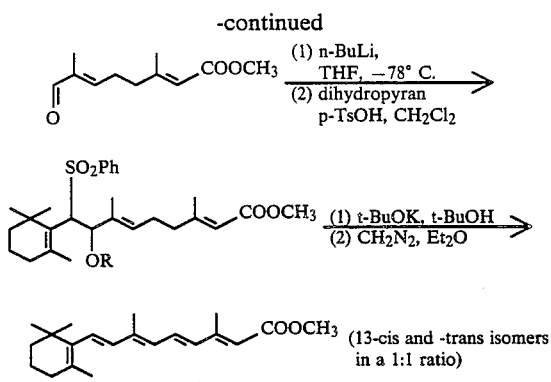

(13-cis and -trans isomers in a 1:1 ratio)

The conventional methods for the production of vitamin A described in (1) to (4) all use beta-ionone as a starting material. The beta-ionone is industrially produced by cyclizing pseudoionone using a large quantity of concentrated sulfuric acid. However, because the yield of beta-ionone is not so high and it is difficult to separate from by-product alpha-ionone, etc. by distillation, betaionone is not always available at low cost.

According to the method of preparing vitamin A acid methyl ester described in (5), the final product is a 1:1 mixture of an all trans-isomer and a 13-cis isomer of vitamin A acid methyl ester despite the fact that the method starts from methyl 7-formyl-3-methyl-2(E),-6(E)-octadienecarboxylate. Hence, reduction in a customary manner of vitamin A acid methyl ester obtained by this method cannot give all trans-vitamin A.

It is an object of this invention to provide an improved process for easily producing vitamin A and its carboxylic acid ester in good yields from readily available cheap industrial materials.

Another object of this invention is to provide an improved process for producing vitamin A and its carboxylic acid ester which are sterically restricted.

Still another object of this invention is to provide novel intermediate compounds which can be advantageously used in the process.

Other objects of this invention along with its advantages will become apparent from the following description which comprises treating a compound represented by the formula

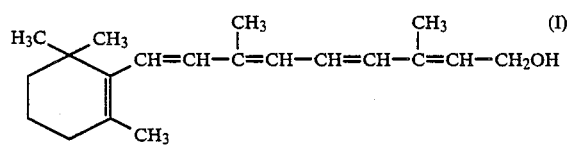

which comprises treating a compound represented by the formula

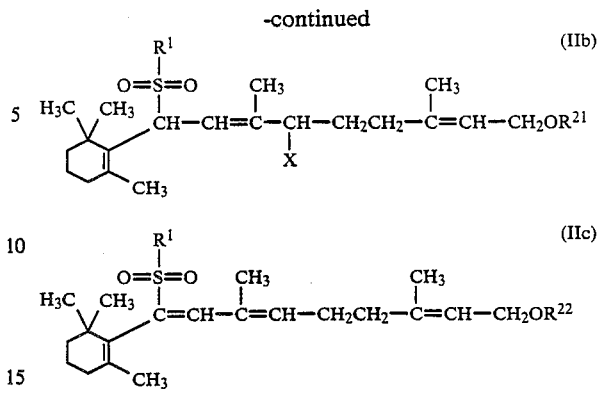

wherein $R^1$ represents an aryl group which may be substituted, $R^{21}$ and $R^{22}$ each represent a hydrogen atom or a lower alkanoyl group, $R^3$ represents an acetal-type protective group for OH, and X represents a halogen atom, with a base.

The term "aryl group which may be substituted", as used herein for $R^1$, means an unsubstituted aryl group or a substituted aryl group having 1 to 5, preferably 1 or 2, substituents. Examples of such substituents include lower alkyl groups such as methyl, ethyl, n-propyl, isopropyl, n-butyl, isobutyl, sec-butyl and tert-butyl, and lower alkoxy groups such as methoxy, ethoxy, n-propoxy, isopropoxy, n-butoxy and tert-butoxy; and halogen atoms such as chlorine, bromine or iodine. Specific examples of the "aryl group which may be substituted" include phenyl, o-tolyl, m-tolyl, p-tolyl, p-ethylphenyl, p-n-propylphenyl, p-isopropylphenyl, p-n-butylphenyl, 2,4-dimethylphenyl, p-methoxyphenyl, 2,4-dimethoxyphenyl, p-chlorophenyl and p-bromophenyl groups. Of these, a phenyl and a p-tolyl group are especially suitable as $R^1$.

The "lower alkanoyl group", as used herein, includes, the example, formyl, acetyl, propionyl and butyryl groups.

The "acetal-type protective group for OH", as used herein, may be any ordinary acetal-type protective group which is used generally for blocking the reactivity of the hydroxy group (OH) in a chemical reaction. Specific examples of the protective group include a tetrahydropyran-2-yl group, a 4-methyl-tetrahydropyran-2-yl group, a tetrahydrofun-2-yl group, and lower alkoxyalkyl groups such as methoxymethyl, 1-methoxyethyl, 1-ethoxyethyl, 1-n-propoxyethyl and 1-n-butoxyethyl groups.

The term "lower", as used herein to qualify a group or compound, means that the group or compound so qualified has not more than 6, preferably not more than 4, carbon atoms. The term "halogen atom", as used herein, means fluorine, chlorine, bromine and iodine atoms. The halogen atom for X is preferably chlorine and bromine.

According to the process of this invention, vitamin A of formula (I) can be obtained by treating the compound of formula (IIa-2), (IIb) or (IIc) with a base. Examples of the base are lower alkoxides of potassium such as potassium methoxide, potassium ethoxide, potassium isopropoxide, potassium n-propoxide, potassium n-butoxide and potassium t-butoxide, and potassium hydroxide.

The amount of the base used is not critical, and can be varied over a wide range according, for example, to the type of the starting material of formula (IIa-2), (II-b) or (IIc) and/or the type of the base. Generally, it may be about 2 to about 30 moles, preferably about 2 to about 10 moles, more preferably about 3 to about 6 moles, per mole of the compound of formula (IIa-2), (IIb) or (IIc)

Usually, the reaction is carried out in a solvent, for example an aliphatic or aromatic hydrocarbon such as hexane, heptane, cyclohexane, benzene or toluene. They may be used either singly or in combination. The amount of the solvent is neither critical. Generally, it is advantageously such that the concentration of the compound (IIa-2), (IIb) or (IIc) in the solvent becomes about 0.05 to about 1 mole, preferably about 0.1 to about 0.5 mole, per liter of solvent.

The temperature at which the aforesaid treatment is carried out may be varied depending, for example, upon the type of the compound (IIa-2), (IIb) or (IIc) and/or the type of the base. Generally, the suitable temperature is about 0° C. to about 100° C., preferably about 20° C. to about 80° C. Usually, the treatment is carried out preferably in an atmosphere of an inert gas such as helium, nitrogen or argon.

By the aforesaid treatment with the base, vitamin A is formed in goods yields from the compound of formula (IIa-2), (IIb) or (IIc). The resulting vitamin A of formula (I) can be isolated and separated from the reaction mixture by methods known per se. For example, water, an aqueous solution of ammonium chloride, etc. are added to the reaction mixture, and the organic layer is separated from the mixture. As required, the organic layer is washed with water and/or dried with anhydrous sodium sulfate, and/or the solvent is evaporated under reduced pressure to separate vitamin A. If required, the product may be subjected to a purifying means such as recrystallization to give vitamin A of high purity.

Vitamin A of formula (II) so obtained can be converted to its carboxylic acid ester by ordinary methods, for example by acylation. The acylation is carried out by reacting the vitamin A-containing organic layer separated from the reaction mixture, or vitamin A separated from the organic layer as above or further purified, with an acylating agent in an organic solvent in the presence of a tertiary amine. The acylating agent may, for example, be acetic anhydride, acetyl chloride, or palmitoyl chloride. The amount of the acylating agent used is preferably about 1 to about 10 equivalents, particularly 1 to 3 equivalents, to vitamin A. Examples of the organic solvent are hydrocarbons such as benzene and toluene, halogenated hydrocarbons such as methylene chloride and 1,2-dichloroethane, ethers such as diethyl ether and diisopropyl ether; and esters such as ethyl acetate and butyl acetate. The organic solvent is used preferably in such an amount as to provide a vitamin A concentration of about 0.1 to about 5 moles/liter. The tertiary amine may, for example, be triethylamine or pyridine. The amount of the tertiary amine is preferably about 1 to about 10 equivalents to vitamin A. By using it in an excessive amount, it can also act as the organic solvent. Conveniently, the acylation is carried out generally at about −10° C. to about 30° C. After the reaction, the precipitate is optionally separated from the reaction mixture by filtration. Then, dilute sulfuric acid, water, a saturated aqueous solution of sodium bicarbonate, or the like is added to the reaction mixture, and the organic layer is separated. The resulting organic layer is optionally subjected to a pre-treatment such as washing with water, drying, or evaporation of the solvent to give a carboxylic acid ester of vitamin A. If required, it is subjected to a purifying means such as recrystallization to give a carboxylic acid ester of vitamin A of high purity.

The compounds of formulae (IIa-2), (IIb) and (IIc) used as the starting material in the above process are novel compounds not described in the prior literature. They can be produced by the following processes.

Compound of formula (IIa-2)

This compound can be produced by steps comprising reacting a compound of the formula

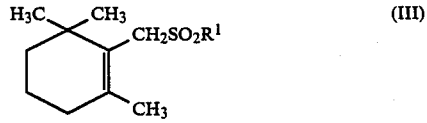

wherein $R^1$ is as defined hereinabove, with a compound of the formula

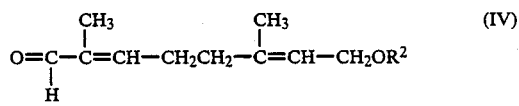

wherein $R^2$ represents a lower alkanoyl group, in the presence of a base to form a compound of the formula

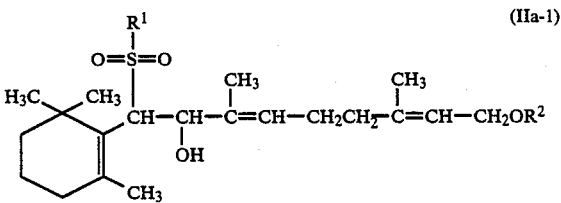

wherein $R^1$ and $R^2$ are as defined above, introducing an acetal-type protective group for OH into this compound, and as required, solvolyzing the resulting compound under non-acidic conditions.

The compound of general formula (III) is used generally in a proportion of about 0.1 to 10 moles, preferably about 1 to 2 moles, per mole of the compound of general formula (IV).

The base to be present in the reaction system during the reaction of compound (III) with the compound (IV) is a base capable of generating a carbanion at the carbon atom to which the group —$SO_2R^1$ is bonded in the compound (III). Specific examples include organolithium compounds such as methyllithium and n-butyllithium; organomagnesium halides (Grignard's reagents) such as methylmagnesium chloride, methylmagnesium bromide, ethylmagnesium chloride and ethylmagnesium bromide; alkali metal hydrides such as lithium hydride, sodium hydride and potassium hydride; alkali metal amides such as lithium amide, sodium amide and potassium amide; and alkali metal (lower) alkoxides such as lithium methoxide, sodium methoxide, potassium methoxide, potassium ethoxide and potassium t-butoxide. The amount of the base is not critical, and can be varied depending upon the type of the base used, etc. Generally, it is about 0.1 to about 1 mole, preferably 0.5 to 1 mole, per mole of the compound of formula (III).

The above reaction is carried out usually in a solvent. The solvent is properly selected, having regard to its combination with the base, from, for example, aliphatic or aromatic hydrocarbons such as hexane, heptane, benzene and toluene, aliphatic or cyclic ethers such as diethyl ether, diisopropyl ether, tetrahydrofuran and dioxane, dimethylformamide, N-methylpyrrolidone, dimethyl sulfoxide and hexamethylphosphoric triamide. The reaction is carried out at a temperature of usually about −100° C. to about 150° C., preferably about −80° C. to about 50° C., although the temperature may be varied depending upon the base used. Advantageously, the reaction is carried out in an atmosphere of an inert gas such as helium, nitrogen or argon. The reaction time may vary depending upon the base, the solvent, the reaction temperature, etc. employed. For example, when the reaction is carried out at temperature of about −80° C. to about −50° C. in tetrahydrofuran using n-butyllithium as the base, the reaction time is about 2 to 6 hours.

The compound of formula (IIa-1) can be separated and recovered from the reaction mixture by ordinary methods. For example, water, an aqueous solution of ammonium chloride, dilute hydrochloric acid, or the like is poured into the reaction mixture, and the organic layer is separated. As required, the organic layer is washed with water and/or dried over anhydrous sodium sulfate, and/or the solvent is evaporated. Then, the product is subjected to a purifying step such as recrystallization or chromatography to isolate the compound of general formula (IIa-1).

The compound of formula (IIa-1) may be converted to a compound of formula (IIa-2) in which $R^{21}$ represents a lower alkanoyl group by, for example, reacting the compound of formula (IIa-1) with a vinyl ether such as 3,4-dihydro2H-pyran, 4-methyl-3,4-dihydro-2H-pyran, 2,3-dihydrofuran, or a lower alkyl vinyl ether such as methyl vinyl ether, ethyl vinyl ether, propyl vinyl ether or butyl vinyl ether in the presence of an acid catalyst; or reacting the compound of formula (IIa-1) with methylal in the presence of phosphorus pentoxide, etc. The reaction of the compound of formula (IIa-1) with the vinyl ether does not necessarily have to be carried out in a solvent. Usually, however, it is preferably carried out in a solvent such as methylene chloride, tetrahydrofuran, diethyl ether or benzene. As the acid catalyst, p-toluenesulfonic acid, its pyridine salt, sulfuric acid, hydrochloric acid, etc. can be used. Toluenesulfonic acid or its pyridine salt is preferably used. When 3,4-dihydro-2H-pyran, 4-methyl-3,4-dihydro2H-pyran or 2,3-dihydrofuran is used as the vinyl ether in this reaction, there can be obtained a compound of formula (IIa-2) in which $R^{21}$ is a lower alkanoyl group and $R^3$ is a tetrahydropyran-2-yl group, a 4-methyl-tetrahydropyran-2-yl group, or a tetrahydrofun-2-yl group, respectively. When the lower alkyl vinyl ether is used as the vinyl ether, a compound of formula (IIa-2) in which $R^{21}$ is a lower alkanoyl group and $R^3$ is a 1-lower alkoxyethyl group is obtained.

On the other hand, by the action of methylal on the compound of formula (IIa-1) in the presence of phosphorus pentoxide or the like, a compound of formula (IIa-2) in which $R^{21}$ is a lower alkanoyl group and $R^3$ is a methoxymethyl group is obtained.

The compound of formula (IIa-2) in which $R^{21}$ represents a lower alkanoyl group obtained by the above reactions can be separated and recovered from the reaction mixture by ordinary methods. For example, water is poured into the reaction mixture, and the mixture is then extracted with an organic solvent such as benzene, diethyl ether, or ethyl acetate. The extract is washed with water, and dried over anhydrous sodium sulfate. Low-boiling substances are evaporated from the extract under reduced pressure, and the residue is chromatographed on a silica gel column. As a result, the compound of formula (IIa-2) in which $R^{21}$ is a lower alkanoyl group can be isolated.

The resulting compound of formula (IIa-2) in which $R^{21}$ represents a lower alkanoyl group can be directly treated with the base. If desired, however, the compound may be solvolyzed under non-acidic conditions and the resulting compound of formula (IIa-2) in which $R^{21}$ represents a hydrogen atom can be treated with the base. Solvolysis of the compound of formula (IIa-1) in which $R^{21}$ represents a lower alkanoyl group may be carried out in a solvent, for example an alcohol such as methanol or ethanol, or a mixture of the alcohol with water and/or a hydrocarbon such as benzene or toluene, preferably in the presence of an alkali metal hydroxide, carbonate or alkoxide. Examples of the alkali metal hydroxide or carbonate are potassium hydroxide, sodium hydroxide, lithium hydroxide, potassium carbonate, potassium methoxide, or sodium methoxide. The amount of the alkali metal hydroxide, carbonate or alkoxide is preferably about 1 to about 2 equivalents to the compound of formula (IIa-2) in which $R^{21}$ is a lower alkanoyl group. The amount of the solvent is preferably such that the concentration of the compound of formula (IIa-2) in which $R^{21}$ is a lower alkanoyl group is about 0.1 to about 10 moles/liter of solvent. When a mixture of an alcohol with water and/or a hydrocarbon is used as the solvent, water and/or the hydrocarbon should desirably be used in such an amount which does not cause phase separation of the reaction system. The reaction is conveniently carried out at a temperature of about −10° C. to about 30° C. The compound of formula (IIa-2) in which $R^{21}$ is a hydrogen atom can be separated from the reaction mixture by ordinary methods. For example, a saturated aqueous solution of ammonium chloride, dilute hydrochloric acid, dilute sulfuric acid, or the like is added to the reaction mixture to neutralize the remaining alkali metal hydroxide or carbonate. As required, the alcohol used as the solvent is evaporated. Water is added to the residue, and the mixture is extracted with an organic solvent such as benzene, methylene chloride, diethyl ether or ethyl acetate. The extract is washed with water and dried over anhydrous sodium sulfate. Thereafter, as required, low-boiling substances are evaporated from the extract under reduced pressure. The residue is chromatographed on a silica gel column whereby a compound of formula (IIa-2) in which $R^{21}$ is a hydrogen atom can be isolated.

The compound of formula (III) used as a starting material in the production of the compound of formula (IIa-2) is a known compound (see Japanese Patent No. 1,168,158), and can be easily produced in good yields from linalool which is a cheap industrial material. For example, a compound of formula (III) in which $R^1$ is a phenyl group can be produced by the following method.

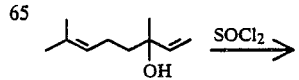

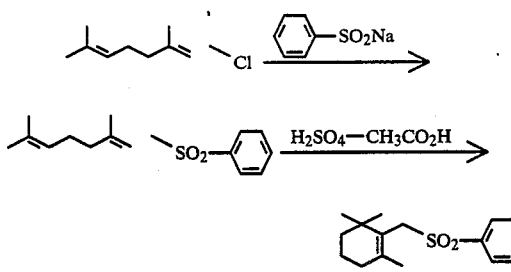

Specifically, the action of thionyl chloride on linalool gives geranyl chloride, and the reaction of geranyl chloride with sodium phenylsulfinate gives geranyl phenyl sulfone. Geranyl phenyl sulfone is cyclized in the presence of an acid catalyst such as a mixed acid of sulfuric acid and acetic acid to give beta-cyclogeranyl phenyl sulfone. In the cyclization reaction, alpha-cyclogeranyl phenyl sulfone, an isomer of beta-cyclogeranyl phenyl sulfone, may sometimes form as a by-product. But beta-cyclogeranyl phenyl sulfone of high purity can be obtained by crystallizing the resulting mixture of the two in a solvent such as hexane. The alpha-cyclogeranyl phenyl sulfone can be converted to beta-cyclogeranyl phenyl sulfone by returning it to the cyclization reaction system. The total yield of beta-cyclogeranyl phenyl sulfone from linalool is usually about 70 to about 90%. The compound of formula (IV), the other starting material, can also be easily produced in good yields from linalool. For example, a compound of formula (IV) in which $R^2$ is an acetyl group can be produced by the following method.

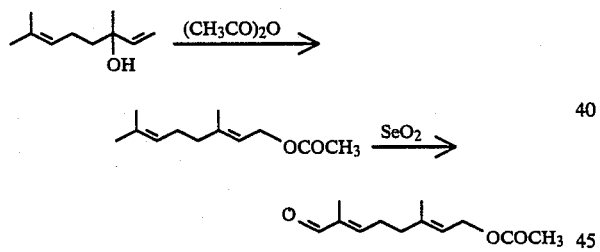

Specifically, the action of acetic anhydride on linalool gives geranyl acetate. The geranyl acetate is reacted, for example, with selenium dioxide in an ethanol solvent under reflux to give the desired 8-acetoxy-2,6-dimethyl-2,6-octadienal. The total yield of 8-acetoxy-2,6-dimethyl-2,6-octadienal from linalool is usually about 60 to about 80%.

The compounds of formulae (IIa-1) and (IIa-2) produced as described above, which are represented by the following formula

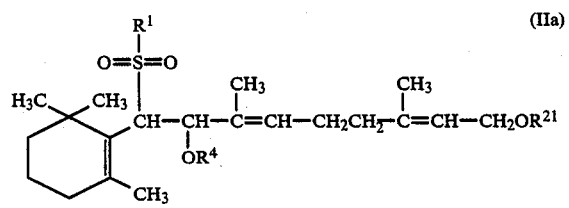

(IIa)

wherein $R^1$ represents an aryl group which may be substituted, $R^{21}$ represents a lower alkanoyl group and $R^4$ represents a hydrogen atom; or $R^{21}$ represents a hydrogen atom or a lower alkanoyl group and $R^4$ represents an acetal-type protective group for a hydroxyl group, are novel compounds not described in the prior literature.

In formula (IIa), $R^1$ is preferably a phenyl or p-tolyl group; $R^{21}$ is preferably a hydrogen atom or an acetyl group; and $R^4$ is preferably a hydrogen atom, a methoxymethyl group, a 1-ethoxyethyl group, a 1-n-butoxyethyl group, a tetrahydropyran-2-yl group or a 4-methyl-tetrahydropyran-2-yl group.

Compound of formula (IIb)

This compound can be produced by halogenating a compound of the formula

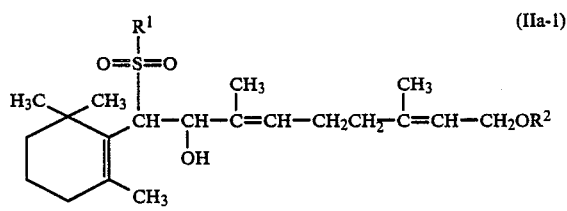

(IIa-1)

wherein $R^1$ and $R^2$ are as defined above, which is obtained as above, and as required, solvolyzing the resulting compound under non-acidic conditions.

Halogenation of the compound of formula (IIa-1) may be carried out by the action of a halogenating agent on it. Examples of the halogenating agent are thionyl halides such as thionyl chloride and thionyl bromide; and halogenated phosphorus compounds such as phosphorus trichloride, phosphorus tribromide, phosphorus pentachloride, and phosphorus oxychloride. The amount of the halogenating agent is not critical, and may be varied depending upon the type of the halogenating agent used. Generally, the suitable amount of the halogenating agent is about 1 to about 10 equivalents, preferably 1 to 3 equivalents, to the compound of formula (IIa-1). The reaction is conveniently carried out in an organic solvent in the presence of a tertiary amine. Examples of the organic solvent are hydrocarbons such as benzene and toluene, halogenated hydrocarbons such as methylene chloride and 1,2-dichloroethane, ethers such as diethyl ether and diisopropyl ether, and esters such as ethyl acetate and butyl acetate. The amount of the solvent is preferably such that the concentration of the compound of formula (IIa-1) is about 0.1 to about 5 moles/liter of solvent. As the tertiary amine, pyridine and triethylamine, for example, can be advantageously used. The tertiary amine is used preferably in an amount of about 0.01 to about 50 equivalents to the compound of formula (IIa-1). but when using it in an excessive amount, the tertiary amine can also act as the organic solvent. The reaction is carried out preferably at a temperature of generally about $-20°$ C. to about $50°$ C., preferably $-10°$ C. to $30°$ C. This reaction yields a compound of formula (IIb) in which $R^{21}$ represents a lower alkanoyl group corresponding to $R^2$ of the starting compound of formula (IIa-1). This compound can be separated from the reaction mixture by ordinary methods. For example, the reaction mixture is poured into water, a saturated aqueous solution of sodium bicarbonate, dilute sulfuric acid, etc. Thereafter, the mixture is extracted with an organic solvent such as benzene, methylene chloride, diethyl ether and ethyl acetate. The extract is washed with water, and dried over anhydrous sodium sulfate. Then, low-boiling substances are evaporated from the extract under reduced pressure. The residue is subjected to a purifying step such as recrystallization or chromatography. As a result, a compound of formula (IIb) in which $R^{21}$ is a lower alkanoyl group can be isolated.

The resulting compound of formula (IIb) in which $R^{21}$ is a lower alkanoyl group may be directly treated with the base. Or if desired, the compound may be solvolyzing under non-acidic conditions and the resulting compound of formula (IIa-2) in which $R^{21}$ is a hydrogen atom can be treated with the base. Solvolysis of the compound of formula (IIa-2) in which $R^{21}$ is lower alkanoyl group may be carried out in the same way as described above.

In the compound of formula (IIb) prepared as above, $R^1$ is preferably a phenyl or p-tolyl group; $R^{21}$ is preferably a hydrogen atom or an acetyl group; and X is preferably a chlorine atom.

Compound of formula (IIc)

This compound can be produced by treating the compound of formula (IIb)( produced as above with a dehydrohalogenating agent.

Examples of the dehydrohalogenating agent that can be used in this reaction include organic or inorganic bases, for example, tertiary amines such as 1,8-diazabicyclo[5.4.0]undec-7-ene, 1,5-diazabicyclo[4.3.0]nona-5-ene, 1,4-diazabicyclo[2.2.2]octane and N-methylmorpholine; and alkali metal hydroxides such as sodium hydroxide and potassium hydroxide. When a compound of formula (IIb) in which $R_{21}$ is a lower alkanoyl group is subjected to the action of the tertiary amine as the dehydrohalogenating agent, a compound of formula (IIc) in which $R^{22}$ is a lower alkanoyl group is obtained. When the alkali metal hydroxide is used as the dehydrohalogenating agent in a solvent containing an alcohol, a compound of formula (IIc) in which $R^{22}$ is a hydrogen atom is obtained. When a compound of formula (IIb) in which $R^{21}$ is a hydrogen atom is reacted with the dehydrohalogenating agent, a compound of formula (IIc) in which $R^{22}$ is a hydrogen atom is obtained. The amount of the dehydrohalogenating agent used is not critical, and may be varied depending upon the type of the dehydrohalogenating agent, the reaction conditions, etc. It is generally about 1 to about 10 moles, particularly 1 to 5 moles, per mole of the compound of formula (IIb). This reaction will usually give advantageous results when carried out in a solvent. The solvent is properly selected having regard to its combination with the dehydrohalogenating agent. When the tertiary amine is used as the dehydrohalogenating agent, the solvent to be used is preferably a hydrocarbon such as benzene and toluene, a halogenated hydrocarbon such as methylene chloride or 1,2-dichloroethane, an ether such as diethyl ether or tetrahydrofuran, or an amide such as N,N-dimethylformamide and N-methylpyrrolidone. The amount of the solvent used is preferably such that the concentration of the compound of formula (IIb) becomes about 0.1 to about 0.1 to about 5 moles/liter of solvent. The reaction is suitably carried out at a temperature of generally about 0° to about 100° C., preferably 20 to 80° C.

When the alkali metal hydroxide is used as the dehydrohalogenating agent, the solvent used is preferably an alcohol such as methanol and ethanol, or a mixture of the alcohol with water and/or a hydrocarbon such as benzene and toluene. The amount of the solvent used in this case is preferably such that the concentration of the compound of formula (IIb) becomes about 0.1 to about 5 moles/liter of solvent. When a mixture of the alcohol with water and/or the hydrocarbon is used as the solvent, the water and/or the hydrocarbon should preferably be used in such an amount which does not cause phase separation of the reaction system. In this case, the reaction is suitably carried out at a temperature of generally about $-20°$ C. to about 50° C., preferably $-10°$ C. to 30° C.

The compound of formula (IIc) obtained by the dehydrohalogenating reaction can be separated from the reaction mixture and purified by ordinary methods. For example, dilute sulfuric acid, an aqueous solution of ammonium chloride, etc. is added to the reaction mixture to neutralize the remaining dehydrohalogenating agent. As required, the solvent is evaporated. Water is added to the residue, and the mixture is extracted with an organic solvent such as benzene, toluene, methylene chloride or ethyl acetate. The extract is washed with water and dried over anhydrous sodium sulfate or the like. The solvent is then evaporated from the extract, and the residue is chromatographed. As a result, the compound of formula (IIc) can be isolated.

A compound of formula (IIc) in which $R^{22}$ is a lower alkanoyl group, which is so obtained, may be converted to a compound of formula (IIc) in which $R^{22}$ is a hydrogen atom by solvolysis under non-acidic conditions. Solvolysis may be carried out as stated hereinabove.

In the compounds of formula (IIc) so produced, $R^1$ is preferably a phenyl or p-tolyl group, and $R^{22}$ is preferably a hydrogen atom or an acetyl group.

The stereochemistry of vitamin A or its carboxylic acid ester produced by the process of this invention depends upon the stereochemistry of the compound of formula (IV)

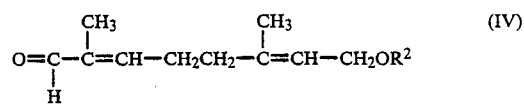

in which $R^2$ is as defined hereinabove. If a compound of formula (IV) in which the stereochemistry based on the carbon-carbon double bonds at the 2- and 6-positions is restricted to trans (E) is used, there is predominantly obtained vitamin A or its carboxylic acid ester which is sterically restricted to all trans. When a compound of formula (IV) in which the stereochemistry based on the carbon-carbon double bond at the 2-position is restricted to trans (E) and that at the 6-position, to cis (Z) is used, there is predominantly obtained vitamin A or its carboxylic acid ester in which the stereochemistry based on the carbon-carbon double bond at the 13-position is restricted to cis.

According to this invention, by reacting the compound of formula (III) and the compound of formula (IV), which are produced easily in good yields from linalool, a cheap industrial material, in the presence of a base, a compound of formula (IIa-1) can be easily produced in high yields. By treating the compound of formula (IIa-2) or the compound of formula (IIb), which are derived from the compound of formula (IIa-1), or the compound of formula (IIc) derived from the compound of formula (IIb) with a base, a sterically restricted vitamin A or its carboxylic acid ester which depends upon the stereochemistry of the compound of formula (IV) can be easily obtained in high yields.

The following Examples illustrate the present invention more specifically. It should be understood however, that these examples in no way restrict the scope of the present invention.

EXAMPLE 1

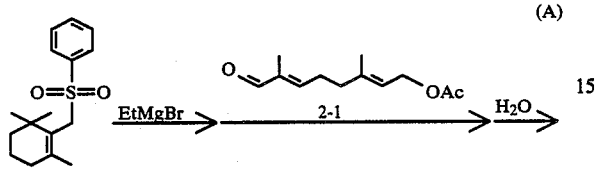

(A)

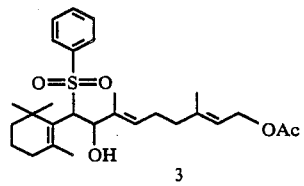

3

A 200 ml three-necked flask purged with nitrogen gas was charged with 10.80 g (38.8 mmoles) of beta-cyclogeranyl phenyl sulfone (1) and 100 ml of toluene, and then 24.2 ml (25.6 mmoles) of a diethyl ether solution of ethyl magnesium bromide (1.06 moles/liter) was added dropwise at an inside temperature of 20° to 25° C. After the addition, the mixture was stirred at 40° to 45° C. for 3 hours. The flask was then cooled so that its inside temperature became −40° to −30° C. To the resulting solution was added dropwise a solution of 4.02 g (19.1 mmoles) of 8-acetoxy-2,6-dimethyl-2(E),6(E)-octadien-1-al (2-1) in 10 ml of toluene. After the addition, the mixture was vigorously stirred at the above temperature for 2 hours. A 10% aqueous solution of hydrochloric acid was added to the reaction mixture, and the toluene layer was separated. The toluene layer was washed with water and then with a saturated aqueous solution of sodium chloride, and dried over anhydrous magnesium sulfate. Toluene was evaporated from the toluene layer, and the residue was chromatographed on a silica gel column using an eluent composed of a 7:3 by volume mixture of hexane and ethyl acetate to give 8.46 g of a colorless transparent oil. By the following analytical data, this product was determined to be a mixture of diastereomers of 1-acetoxy-8-hydroxy-3,7-dimethyl-9-(2,6,6-trimethyl-1-cyclohexen-1-yl)-9-phenylsulfonyl-2(E),6(E)-nonadiene (3).

Yield 91%.

NMR δ CDCl$_3$(CH$_3$)$_3$SiOSi(CH$_3$)$_3$: 0.61–2.03 (m, 28H); 2.87 (br, 1H); 3.95, 4.20 (d. 1H in total); 4.50 (d, 2H); 4.85, 4.97 (d, 1H in total); 5.25, 5.62 (m, 2H in total); 7.40–8.03 (m, 5H).

IR (film) ν (cm$^{-1}$): 3500 (OH), 1735 (C=O), 1140 (SO$_2$).

FD-MASS m/e: 488 (M$^+$).

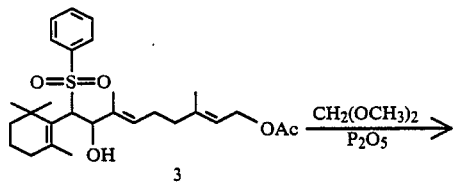

(B)

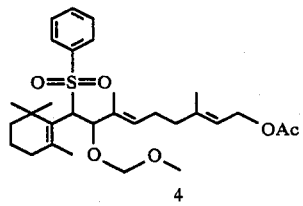

4

A 100 ml flask was charged with 2.67 g (5.5 mmoles) of compound (3) and 9.65 ml (110 mmoles) of methylal, and the mixture was stirred to form a solution. To the solution was added 0.22 g (1.54 mmoles) of phosphorus pentoxide, and the mixture was stirred at room temperature. Two hours and 5 hours later respectively, 0.21 g of phosphorus pentoxide was added, and the reaction was carried out for 24 hours.

A saturated aqueous solution of sodium bicarbonate was put in a separating funnel, and the solution portion of the reaction mixture was added to it. Toluene and a saturated aqueous solution of sodium bicarbonate were added to the residue, and the mixture was stirred whereby the tarry material dissolved. The resulting aqueous layer and organic layer were transferred to the separating funnel. The separated organic layer was washed with a saturated aqueous solution of sodium bicarbonate and dried over anhydrous magnesium sulfate.

The anhydrous magnesium sulfate was removed by filtration, and the solvent was evaporated at 40° C. to give a red oily product. The oily product was chromatographed on a silica gel column using an eluent composed of a mixture of ethyl acetate and n-hexane in a ratio of from 1:6 to 1:4 to give 2.68 g of a yellow oil. By the following analytical data, this product was determined to be 1acetoxy-3,7-dimethyl-8-methoxymethoxy-9-phenylsulfonyl-9(2,6,6-trimethyl-1-cyclohexen-1-yl)-2(E),6(E)-nonadiene (4). Yield 92%.

NMR δ CDCl$_3$(CH$_3$)$_3$SiOSi(CH$_3$)$_3$: 0.69–1.99 (m, 28H); 3.16, 3.35 (s, 3H); 3.96–5.60 (m, 8H); 7.38–8.01 (m, 5H).

IR (film) ν (cm$^{-1}$): 1730 (C=O), 1140 (SO$_2$).

FD-MASS m/e: 532(M$^+$).

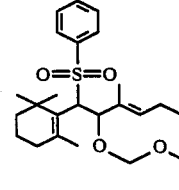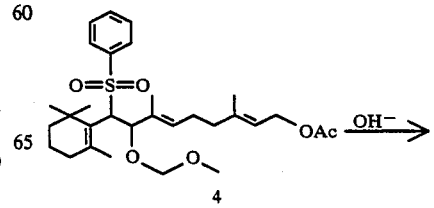

(C)

4

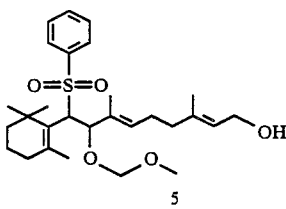

A 100 ml flask was charged with 2.68 g of compound (4) and 11 ml of methanol, and the mixture was stirred to form a solution. Sodium hydroxide (0.33 g) was added, and the mixture was stirred at room temperature for 1.5 hours. The reaction mixture was transferred to a separating funnel, and a large amount of water and toluene were added to extract the mixture with toluene. The toluene extract was washed with a saturated aqueous solution of ammonium chloride and water, and dried over anhydrous magnesium sulfate. The anhydrous magnesium sulfate was removed by filtration, and toluene was evaporated at 40° C. under reduced pressure to give a red oily product. The oily product was chromatographed on a silica gel column using an eluent composed of a mixture of ethyl acetate and n-hexane in a ratio of from 1:1 to 1:4 to give 2.34 g of a yellow oil. By the following analytical data, this product was determined to be 1-hydroxy-3,7-dimethyl-8-methoxymethoxy-9-phenylsulfonyl-9-(2,6,6-trimethyl-1-cyclohexenl-yl)-2(E),6(E)-nonadiene (5).

NMR δ CDCl$_3$(CH$_3$)$_3$SiOSi(CH$_3$)$_3$: 0.68–2.04 (m, 26H); 3.15, 3.35 (s, 3H); 3.95–5.60 (m, 8H); 7.40–8.00 (m, 5H).

IR (film) ν (cm$^{-1}$): 3500 (C=O), 1140 (SO$_2$).

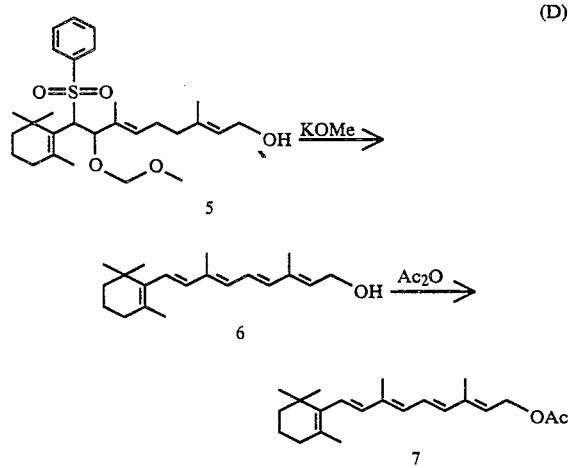

Under a nitrogen gas atmosphere, a 50 ml brown flask was charged with 0.5121 g (1.05 mmoles) of compound (5) and 5 ml of toluene, and the mixture was stirred to form a solution. To the solution was added 0.21 g (3.15 mmoles) of potassium methoxide, and the mixture was stirred at room temperature for 5 minutes and further at 40° C. for 2 hours.

Hexane (20 ml) and 15 ml of water were added to the reaction mixture, and the mixture was transferred to a separating tunnel. The separated aqueous layer was extracted with 15 ml of hexane, and the extract was combined with the hexane layer. The mixture was washed twice with water, and dried over anhydrous magnesium sulfate. The anhydrous magnesium sulfate was removed by filtration, and the solvent was evaporated at 35° C. under reduced pressure to give an orange oily product. The IR spectrum of this product agreed with that of commercial vitamin A (6).

Under a nitrogen atmosphere, a 100 ml brown flask was charged with the oily product obtained above, 4 ml of hexane and 1.1 ml of triethylamine, and cooled with an ice water bath. Acetic anhydride (0.68 ml) was added, and the mixture was stirred at the same temperature for 20 minutes and further at room temperature for 16 hours.

Hexane (25 ml) was added to the reaction mixture, and the mixture was cooled with an ice water bath. Then, 10 ml of a saturated aqueous solution of sodium bicarbonate was added. The mixture was stirred for 15 minutes and transferred to a separating funnel. It was separated by adding 15 ml of hexane and 10 ml of a saturated aqueous solution of sodium bicarbonate. The hexane layer was washed with a saturated aqueous solution of sodium bicarbonate, and dried over anhydrous magnesium sulfate.

The anhydrous magnesium sulfate was removed by filtration, and the solvent was evaporated at 35° C. under reduced pressure to give 0.3723 g of an orange oily product. By high-performance liquid chromatography (column: μ-porasil; mobile phase: a 9:1 mixture of hexane and diisopropyl ether), the oily product was found to contain 0.2755 g (all-trans content: 95%) of vitamin A acetate (7). The total yield based on the compound (5) was 80%.

EXAMPLE 2

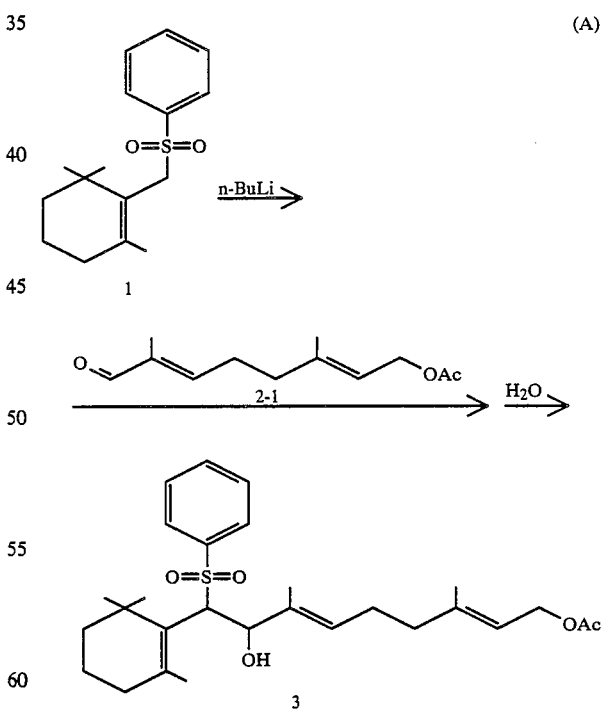

A 200 ml flask purged with argon gas was charged with 5.00 g (18.0 mmole) of beta-cyclogeranyl phenyl sulfone (1) and 60 ml of tetrahydrofuran, and cooled to −78° C. Then, 6.6 ml (9.9 mmoles) of a hexane solution of n-butyllithium (1.5 moles/liter) was added dropwise, and the mixture was stirred at the above temperature for 3 hours. Then, a solution of 1.89 g (9.0 mmoles) of 8-acetoxy-2,6-dimethyl-2(E),6(E)-octadien-1-al(2-1) in 15 ml of tetrahydrofuran was added dropwise at −78° C., and the mixture was stirred at this temperature for 2 hours and further at −50° C. for 2 hours. The reaction mixture was cooled to −78° C., and water was added to it. The temperature of the mixture was then raised to room temperature. The mixture was extracted with three 100 ml portions of benzene. The extracts were washed with water, and dried over anhydrous sodium sulfate. Benzene was evaporated from the extracts, and the residue was chromatographed on a silica gel column using an eluent composed of a 5:1 by volume mixture of hexane and ethyl acetate to give 4.01 g of a colorless transparent oil By the following analytical data, the product was determined to be 1-acetoxy-8-hydroxy-3,7-dimethyl- 9-(2,6,6-trimethyl-1-cyclohexen-1-yl)-9-phenylsulfonyl-2(E),6(E)-nonadiene(3). Yield 93%.

NMR δ CDCl$_3$(CH$_3$)$_3$(SiOSi(CH$_3$)$_3$: 0.62–1.94 (m, 28H); 3.73 (br, 1H); 3.81 (d, 1H); 4.41 (d, 2H); 4.90 (d, 1H); 5.21 (m, 2H); 7.38–7.00 (m, 5H).

IR (film) ν (cm$^{-1}$): 3500 (OH), 1735 (C=O), 1140 (SO$_2$).

FD-MASS m/e: 488 (M+).

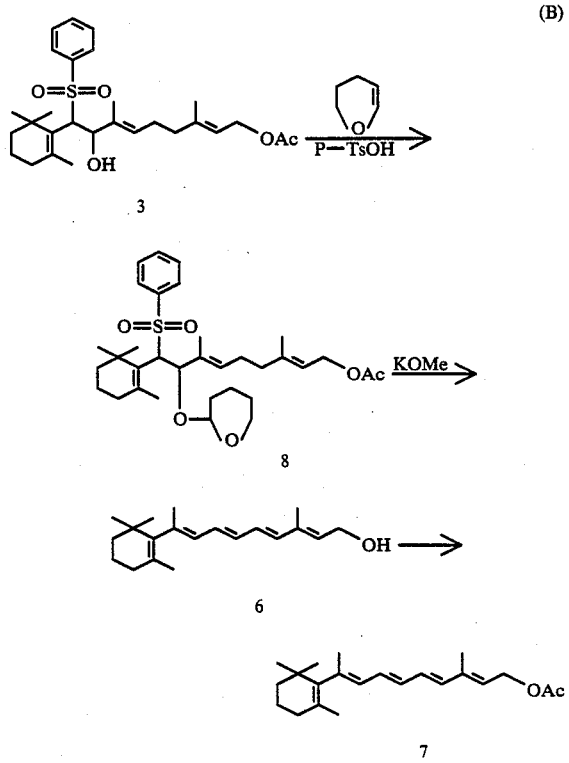

(B)

3

8

6

7

A 100 ml flask was charged with 1.36 g (2.8 mmoles) of 1-acetoxy-3,7-dimethyl-8-hydroxy-9-phenylsulfonyl-9-(2,6,6-trimethyl-1-cyclohexen-1-yl)-2(E),6(E)-nonadiene (3), a catalytic amount of pyridinium p-toluenesulfonate and 15 ml of methylene chloride, and cooled with an ice water bath. To the solution was added dropwise 0.73 ml (8.4 mmoles) of 3,4-dihydro-2H-pyran, and the mixture was stirred for 3 hours with cooling in the bath. An aqueous sodium bicarbonate solution was poured into the reaction mixture, and the mixture was extracted with methylene chloride. The methylene chlorine extract was washed with water, and dried over anhydrous sodium sulfate. Methylene chloride was evaporated from the extract by an evaporator, and the remaining oil was chromatographed on a silica gel column using an eluent composed of a 1:5 mixture of ethyl acetate and n-hexane to give 1.59 g of 1-acetoxy-3,7-dimethyl-8-(tetrahydropyran-2-yl)oxy-9phenylsulfonyl-9-(2,6,6-trimethyl-1-cyclohexen-1-yl)2(E),6(E)-nonadiene (8). Yield 99%. The analytical data of the product were as follows:

NMR δ CDCl$_3$(CH$_3$)$_3$SiOSi(CH$_3$)$_3$: 0.62–2.03 (m, 34H); 3.23–5.36 (m, 9H); 7.43–8.15 (m, 5H).

IR (film) ν (cm$^{-1}$): 1150 (SO$_2$).

FD-MASS m/e: 573 (M++1), 572 (M+).

Under a nitrogen gas atmosphere, a 100 ml brown flask was charged with 1.59 g of compound (8) and 15.9 ml of toluene, and the mixture was stirred to form a solution. While the inside temperature was maintained at 27° C., 0.97 g of potassium methoxide was added. The mixture was stirred at this temperature for 0.3 hour, and then at an inside temperature of 38° C. for 1.5 hours.

Hexane (60 ml) and 45 ml of water were added to the reaction mixture, and the hexane layer was separated by a separating funnel. The aqueous layer was extracted with 45 ml of hexane, and the extract was combined with the separated hexane layer. The mixture was washed twice with water, and dried over anhydrous magnesium sulfate. The anhydrous magnesium sulfate was removed by filtration, and the solvent was evaporated at 35° C. under reduced pressure to give an orange oily product (6).

Under a nitrogen gas atmosphere, a 100 ml brown flask was charged with the above oily product (6), 10.6 ml of hexane and 2.9 ml of triethylamine, and cooled with an ice water bath. Acetic anhydride (1.8 ml) was added, and the mixture was stirred at the same temperature for 20 minutes and further at room temperature for 16 hours.

Hexane (70 ml) was added to the reaction mixture, and the mixture was cooled with an ice water bath. To the mixture was added 27 ml of a saturated aqueous solution of sodium bicarbonate, and the mixture was stirred for 15 minutes. The reaction mixture was transferred to a separating funnel, and separated by adding 40 ml of hexane and 27 ml of a saturated aqueous solution of sodium bicarbonate. The hexane layer was washed with a saturated aqueous solution of sodium bicarbonate, and dried over anhydrous magnesium sulfate.

The anhydrous magnesium sulfate was removed by filtration, and the solvent was evaporated at 35° C. under reduced pressure to give an orange-colored oily product. By high-performance liquid chromatography (column: μ-porasil; mobile phase: a 9:1 mixture of hexane and diisopropyl ether), this product was found to contain 0.70 g (all trans content: 95%) of vitamin A acetate (7). The yield of the product based on compound (8) was 77%.

EXAMPLE 3

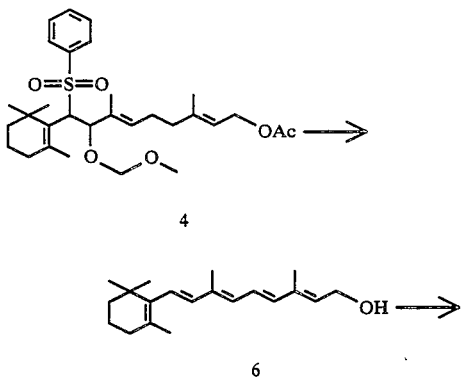

Under a nitrogen gas atmosphere, a 100 ml brown flask was charged with 2.68 g of 1-acetoxy-3,7-dimethyl-8-methoxymethoxy-9-phenylsulfonyl-9-(2,6,6-trimethyl-1-cyclohexen-1-yl)-2(E),6(E)-nonadiene(4) obtained in Example 1, (B) and 80 ml of cyclohexane, and the mixture was stirred to form a solution. Then, 3.53 g of potassium methoxide was added, and the mixture was stirred at an inside temperature of 39° C. for 1.8 hours.

Hexane (96 ml) and 72 ml of water were added to the reaction mixture, and the mixture was transferred to a separating funnel. The aqueous layer separated was extracted with 96 ml of hexane, and the extract was combined with the separated hexane layer. The mixture was washed twice with water, and then dried over anhydrous magnesium sulfate. The anhydrous magnesium sulfate was removed by filtration, and the solvent was evaporated at 35° C. under reduced pressure to give an orange-colored oily product.

Under a nitrogen gas atmosphere, a 300 mol brown flask was charged with the above oily product, 19.2 ml of hexane and 5.3 ml of triethylamine, and cooled with an ice water bath. Acetic anhydride (3.26 ml) was added, and the mixture was stirred at this temperature for 20 minutes and further at room temperature for 16 hours. Hexane (120 ml) was added to the reaction mixture, and the mixture was cooled with an ice water bath. Then, 48 ml of a saturated aqueous solution of sodium bicarbonate was added, and the mixture was stirred for 15 minutes. The mixture was then transferred to a separating funnel, and 72 ml of hexane and 48 ml of an aqueous sodium bicarbonate solution was added to separate the mixture into layers. The hexane layer was washed with a saturated aqueous solution of sodium bicarbonate, and dried over anhydrous magnesium sulfate.

The magnesium sulfate was removed by filtration, and the solvent was evaporated at 35° C. under reduced pressure to give an orange-colored oily product. By high-performance liquid chromatography (column: μ-porasil; mobile phase: a 9:1 mixture of hexane and diisopropyl ether), this product was found to contain 1.29 g (all-trans content: 95%) of vitamin A acetate (7). The yield of the product based on the compound (4) was 78%.

EXAMPLE 4

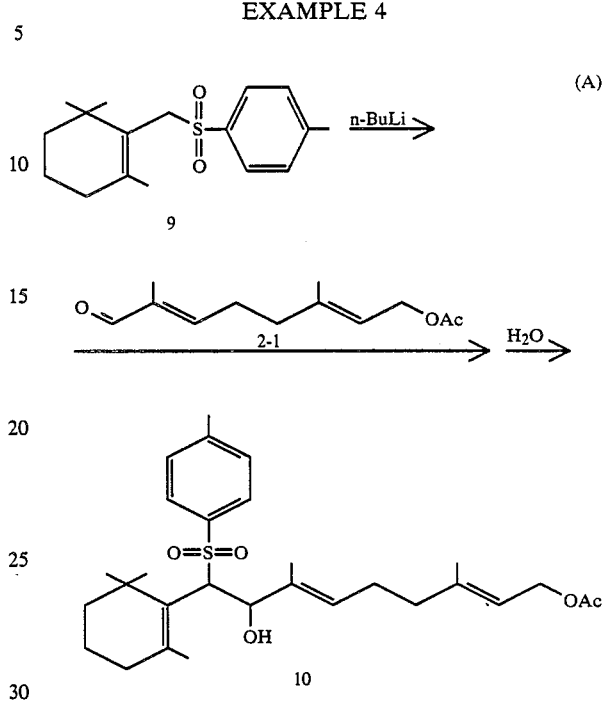

A 200 ml three-necked flask purged with argon gas was charged with 7.01 g (24.0 mmoles) of beta-cyclogeranyl p-tolyl sulfone and 70 ml of tetrahydrofuran, and cooled to $-78°$ C. Then, 9.6 ml (14.4 mmoles) of a hexane solution of n-butyllithium (1.5 moles/liter) was added dropwise, and the mixture was stirred at the above temperature for 2 hours. A solution of 2.52 g (12.0 mmoles) of 8-acetoxy2,6-dimethyl-2(E),6(E)-octadien-1-al (2-1) in 15 ml of tetrahydrofuran was added dropwise to the solution at $-78°$ C., and the mixture was stirred at this temperature for 3 hours. Water was added to the reaction mixture, and the temperature of the mixture was raised to room temperature. The mixture was extracted successively with three 50 ml portions of benzene. The benzene extracts were washed with water, and dried over anhydrous magnesium sulfate. The solvent was evaporated from the extracts, and the residue was chromatographed on a silica gel column using an eluent composed of a mixture of hexane and ethyl acetate in a volume ratio of from 5:1 to 3:1 to give 4.88 g of a white solid. By the following analytical data, this product was determined to be 1-acetoxy-8-hydroxy-3,7-dimethyl-9-(2,6,6-trimethyl-1-cyclohexen-1-yl)-9-(p-tolyl)sulfonyl-2(E),6(E)-nonadiene (10). Yield 81%.

NMR δ CDCl$_3$(CH$_3$)$_3$ SiOSi(CH$_3$)$_3$: 0.61–2.01 (m, 28H); 2.37 (s, 3H); 3.71 (br., 1H); 3.94 (d, 1H); 4.49 (d, 2H); 4.97 (d, 1H); 5.16 (m, 2H); 7.26 (d, 2H); 7.86 (d, 2H).

IR (film) ν (cm$^{-1}$): 3480 (OH), 1735 (C=O), 1140 (SO$_2$).

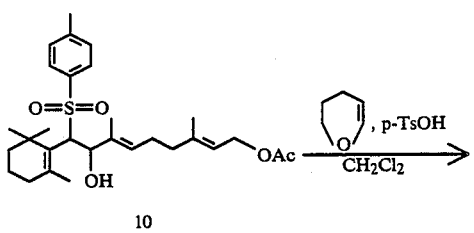

10

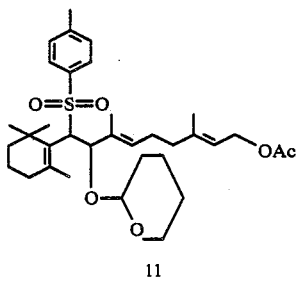

11

A 100 ml flask was charged with 1.00 g (1.99 mmoles) of compound (10), 0.52 ml of 3,4-dihydro-2H-pyran, 10 ml of methylene chloride, and a catalytic amount of p-toluenesulfonic acid, and the mixture was stirred at 0° C. for 6 hours.

A saturated aqueous solution of sodium bicarbonate was put in a separating funnel, and the solution portion of the reaction mixture was added to it. The methylene chloride layer was separated. The aqueous layer was extracted with methylene chloride, and the extract was combined with the separated methylene chloride layer. The mixture was washed with water and dried over anhydrous magnesium sulfate.

The magnesium sulfate was removed by filtration, and methylene chloride was evaporated by an evaporator to give 1.47 g of a viscous oil. The oil was chromatographed on a silica gel column using an eluent composed of a 1:3 mixture of ethyl acetate and hexane to give 1.09 g of a product. By the IR analysis, this product was determined to be 1-acetoxy-3,7-dimethyl-8-(tetrahydropyran-2-yl)oxy-9-(p-tolyl)sulfonyl-9-(2,6,6-trimethyl-2-cyclohexen-1-yl)-2(E),6(E)-nonadiene (11). Yield 93%.

IR (film) ν (cm⁻¹): 2930, 1740, 1600, 1450, 1380, 1365, 1300, 1230, 1140, 1080, 1020, 960, 815.

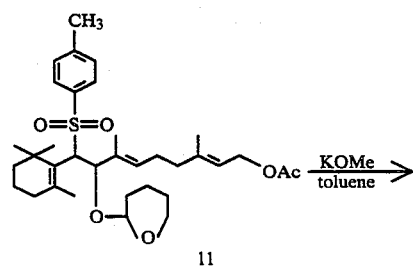

11

(B)

(C)

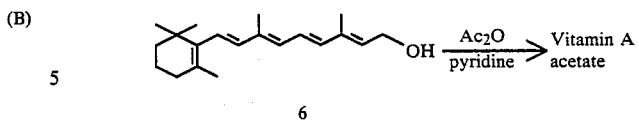

6

A 100 ml brown flask was charged with 0.60 g (8.53 mmoles) of potassium methoxide and 25 ml of toluene, and in an argon atmosphere, a solution of 1.00 g (1.71 mmoles) of compound (11) in 5 ml of toluene was added at room temperature. The mixture was stirred at room temperature for 30 minutes, and further at 40° C. for 2 hours.

The reaction mixture was poured into an aqueous solution of ammonium chloride, and extracted with diethyl ether. The extract was washed with water and then with a saturated aqueous solution of sodium chloride, and dried over anhydrous magnesium sulfate. The magnesium sulfate was removed by filtration, and then the diethyl ether and toluene were evaporated to give 0.76 g of a reddish yellow oil (6).

The oil was dissolved in 5 ml of pyridine, and 5 ml of acetic anhydride and a analytic amount of dimethylaminopyridine were added. The mixture was stirred at room temperature for 2 hours.

The reaction mixture was poured into a large amount of water, and extracted with n-hexane. The hexane extract was washed with an 80% aqueous solution of methanol and further three times with water, and dried over anhydrous magnesium sulfate. The anhydrous magnesium sulfate was removed by filtration, and n-hexane was evaporated to give 0.64 g of a reddish yellow oil. By liquid chromatography, this oil was found to contain 0.34 g (all-trans content: 95%) of vitamin A acetate. The total yield of the product based on the compound (11) was 61%.

EXAMPLES 5-7

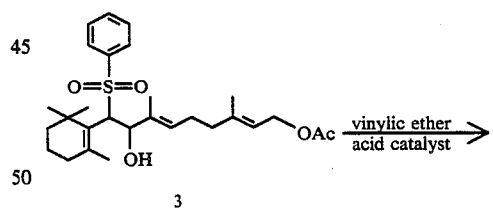

3

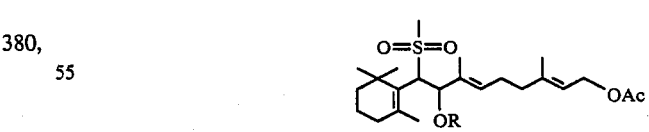

12-14

1.36 g (2.8 mmoles) of 1-acetoxy-3,7-dimethyl-8-hydroxy-9-phenylsulfonyl-9-(2,6,6-trimethyl-1-cyclohexen-1-yl)-2(E),6(E)-nonadiene (3) obtained in Example 2 in 15 ml of methylene chloride was subjected to the following reaction conditions, and the reaction mixture was worked up in the same way as in Example 2 to give the corresponding acetals. The results are shown in the following table.

| Example | Vinylic ether (mole ratio to 3) | Acid catalyst (mole ratio to 3) | Reaction temperature (°C.) | Reaction time (hours) | R (Comp. No.) | Yield (%) |
|---|---|---|---|---|---|---|
| 5 | 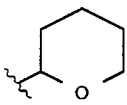 (1.5) | p-TsOH H₂O (0.01) | 5 | 2.4 | (12) | 99 |
| 6 | 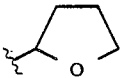 (1.5) | p-TsOH H₂O (0.01) | 5 | 2.4 | (13) | 97 |
| 7 | 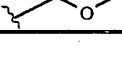 (2.0) | p-TsOH pyridine (0.04) | 26 | 5.8 | (24) | 94 |

EXAMPLES 8–10

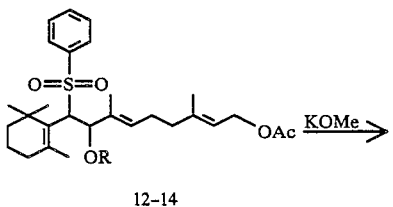

12–14

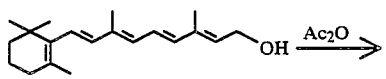

6

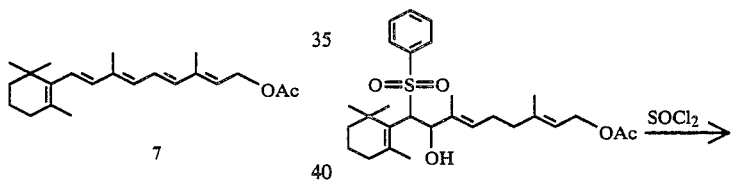

7

The same reaction as in Example 1 was carried out under the conditions shown in the following table using 1.05 mmoles of each of the compounds (12), (13) and (14) obtained in Examples 5 to 7 to obtain vitamin A acetate (7). The results are shown in the following table.

| Example | Compound No. | Potassium methoxide (mole ratio) | Toluene (ml) | Reaction temperature and time | Yield of vitamin A acetate (total from 12–14) | All-trans content (%) |
|---|---|---|---|---|---|---|
| 8 | 12 | 5.0 | 6.0 | (1) at 27° C. for 0.3 hour (2) at 38° C. for 1.5 hours | 78 | 95 |
| 9 | 13 | 5.0 | 5.7 | " | 74 | 95 |
| 10 | 14 | 5.0 | 4.7 | (1) at 25° C. for 0.3 hour (2) at 39° C. for 1.5 hours | 83 | 95 |

EXAMPLE 11

0.76 g of the reddish yellow oil (6) obtained by the reaction of compound (11) with potassium methoxide in toluene in Example 4 was dissolved in 5 ml of pyridine, and the solution was cooled with ice water. Then, 0.71 g (2.58 mmoles) of palmitoyl chloride was added to the solution, and the mixture was stirred at the same temperature for 0.5 hour, the further at room temperature for 5 hours.

The reaction mixture was poured into a large amount of water, and extracted with n-hexane. The hexane extract was washed three times with water, and dried over anhydrous magnesium sulfate. The magnesium sulfate was removed by filtration, and hexane was evaporated under reduced pressure to give 0.73 g of reddish yellow oil. By liquid chromatography (column: μ-porasil: mobile phase: a 2:98 mixture of diisopropyl ether and hexane), this oil was found to contain 0.55 g (all-trans content: 95%) of vitamin A palmitate.

EXAMPLE 12

(A)

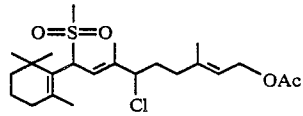

3

[structure]

15

A 100 ml flask was charged with 7.38 g (15 mmoles) of 1-acetoxy-8-hydroxy-3,7-dimethyl-9-(2,6,6,-trimethyl-1-cyclohexen-1-yl)-9-phenylsulfonyl-2(E),6(E)- nonadiene (3) obtained in Example 1, (A), 60 ml of benzene and 12 ml of pyridine, and while the flask was cooled on an ice water bath, 1.32 ml of thionyl chloride was added dropwise. Then, the mixture was stirred at room temperature for 16 hours. A 3% aqueous solution of sulfuric acid cooled with ice was added to the reaction mixture, and the organic layer was separated. The aqueous layer was extracted with two 70 ml portions of diethyl ether. The extracts were combined with the organic layer, and the mixture was successively washed with a 3% aqueous sulfuric acid solution cooled with ice, a saturated aqueous solution of sodium bicarbonate and a saturated aqueous solution of sodium chloride, and dried over anhydrous magnesium sulfate. The solvent was evaporated from the organic layer. The residue was chromatographed on a silica gel column using an eluent composed of a 5:1 by volume mixture of hexane and ethyl acetate to give 7.18 g of a white waxy product. By the following analytical data, this product was determined to be 1-acetoxy-6-chloro-3,7-dimethyl-9-(2,6,6-trimethyl-1-cyclohexen-1-yl)-9-phenylsulfonyl-2,7-nonadiene (15). Yield 94%.

NMR δ CDCl$_3$(CH$_3$)$_3$/CDCl$_3$ SiOSi(CH$_3$)$_3$: 0.72–2.05 (m, 28H); 4.17–4.57 (m, 4H); 5.23 (t, 1H); 5.88 (m, 1H); 7.35–7.91 (m, 5H).

IR (film) ν (cm$^{-1}$): 1745 (C=O), 1150 (SO$_2$), 685 (C$_6$H$_5$).

RD-MASS m/e: 506 (M$^+$), 507 (M$^+$+1), 470 (M$^+$—HCl), 365 (M$^+$—C$_6$H$_5$SO$_2$).

(B)

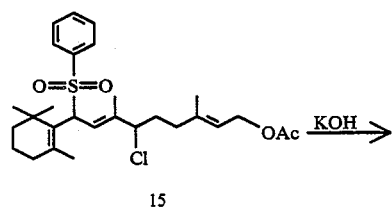

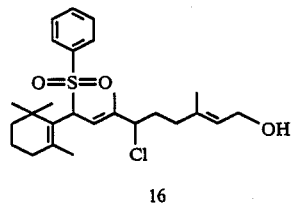

A 10 ml flask was charged with 0.0226 g (0.342 mmole) of potassium hydroxide having a purity of 85% and 1 ml of methanol. The mixture was stirred at room temperature to prepare a methanol solution of potassium hydroxide. To the solution was added a solution of 0.0373 g (0.0736 mmole) of 1-acetoxy-6-chloro-3,7-dimethyl-9-(2,6,6-trimethyl-1-cyclohexen-1-yl)-9-phenylsulfonyl-2,7-nonadiene (15) in a mixture of 2 ml of methanol and 0.2 ml of benzene. The mixture was stirred in an ice water bath for 30 minutes. A saturated aqueous solution of ammonium chloride was added to the reaction mixture, and the solvent was evaporated from it. Water was added to the residue, followed by extraction with diethyl ether. The extract was washed with a saturated aqueous solution of ammonium chloride, and dried over anhydrous magnesium sulfate. The solvent was evaporated from the extract to give 0.0297 g of a yellow oil. By the following analytical data, this product was identified as 6-chloro-1-hydroxy-3,7-dimethyl-9-(2,6,6-trimethyl-1-cyclohexen-1-yl)-9-phenylsulfonyl-2,7-nonadiene (16). Yield 87%.

NMR δ CDCl$_3$(CH$_3$)$_3$SiOSi(CH$_3$)$_3$:/CDCl$_3$ 0.75–2.20 (m, 26H); 4.06 (d, 2H); 4.21–4.55 (m, 2H); 5.30 (t, 1H); 5.91 (m, 1H); 7.36–7.90 (m, 5H).

IR (film) ν (cm$^{-1}$): 3300 (OH), 1150 (SO$_2$), 685 (C$_6$H$_5$).

FD-MASS m/e: 465 (M$^+$+1), 428 (M$^+$—HCl), 323 (M$^+$—C$_6$H$_5$SO$_2$).

EXAMPLE 13

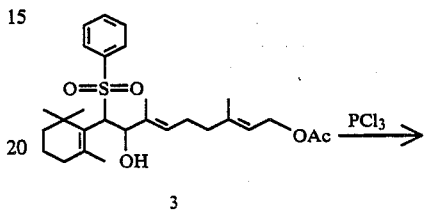

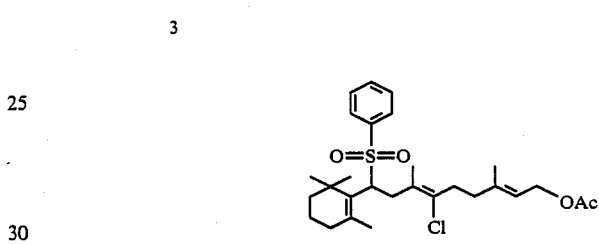

A 50 ml flask was charged with 2.44 g (5.00 mmoles) of 1-acetoxy-8-hydroxy-3,7-dimethyl-9-(2,6,6-trimethyl-1-cyclohexen-1-yl)-9-phenylsulfonyl-2(E),6(E)-nonadiene (3), 0.12 g of pyridine and 20 ml of methylene chloride. While the flask was cooled with an ice water bath, 0.29 ml (3.3 mmoles) of phosphorus trichloride was added dropwise. The mixture was then stirred at the above temperature for 6 hours. To the reaction mixture was added a saturated aqueous solution of sodium bicarbonate, and the mixture was extracted with diethyl ether. The extract was washed with a saturated aqueous solution of sodium bicarbonate, and dried over anhydrous magnesium sulfate. The solvent was evaporated from the extract, and the residue was chromatographed on a silica gel column using an eluent composed of a mixture of hexane and ethyl acetate in a volume ratio of from 9:1 to 5:1 to give 1.27 g (yield 50%) of 1-acetoxy-6-chloro-3,7-dimethyl-9-(2,6,6-trimethyl-1-cyclohexen-1-yl)-9-phenylsulfonyl-2,7-nonadiene (15).

EXAMPLE 14

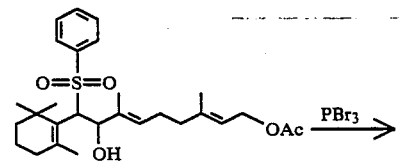

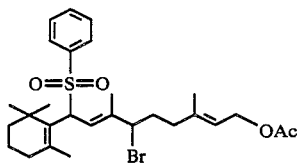

17

A 50 ml flask was charged with 2.44 g (5.0 mmoles) of 1-acetoxy-8-hydroxy-3,7-dimethyl-9-(2,6,6-trimethyl-1-cyclohexen-1-yl)-9-phenlsulfonyl-2(E),6(E)-nonadiene (3) obtained in Example 2, (A), 0.12 g of pyridine and 20 ml of methylene chloride, and while the flask was cooled with an ice water bath, 0.31 ml (3.3 mmoles) of phosphorus tribromide was added dropwise, and the mixture was stirred at this temperature for 1.5 hours. To the reaction mixture was added a saturated aqueous solution of sodium bicarbonate, followed by extraction with diethyl ether. The extract was washed successively with a saturated aqueous solution of sodium bicarbonate and a saturated aqueous solution of sodium chloride, and dried over anhydrous magnesium sulfate. The solvent was evaporated from the extract, and the residue was chromatographed on a silica gel column using an eluent composed of a mixture of hexane and ethyl acetate in a volume ratio of the from 9:1 to 3:1 to give 2'34 g of a white waxy product. By the following analytical data, this product was determined to be 1-acetoxy-6-bromo-3,7-dimethyl-9-(2,6,6-trimethyl-1-cyclohexen-1-yl)-9-phenylsulfonyl-2,7-nonadiene (17). Yield 85%.

NMR δ CDCl$_3$(CH$_3$)$_3$SiOSi(CH$_3$)$_3$: 1.71–2.03 (m, 28H); 4.32–4.57 (m, 4H); 5.24 (m, 1H); 5.90 (m, 1H); 7.43–7.90 (m, 5H).

IR (film) ν (cm$^{-1}$): 1730 (C=O), 1135 (SO$_2$), 670 (C$_6$H$_5$).

FD-MASS m/e: 550 (M+), 470 (M+—HBr), 409 (M+—C$_6$H$_5$SO$_2$).

EXAMPLE 15

(A)

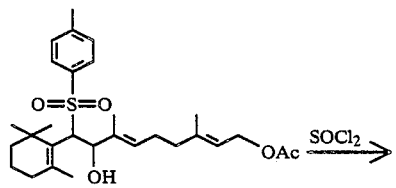

10

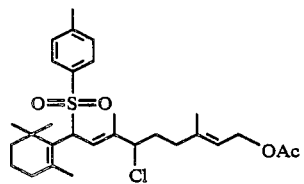

18

A 50 ml flask was charged with 610 mg (1.26 mmoles) of 1-acetoxy-8-hydroxy-3,7-dimethyl-9-(2,6,6-trimethyl-1-cyclohexen-1-yl)-9-(p-tolyl)sulfonyl-2(E),6(E)-nonadiene (10) obtained in Example 4, (A), 0.96 ml (12 mmoles) of pyridine and 15 ml of benzene. While the flask was cooled with an ice water bath, 0.11 ml (1.5 mmoles) of thionyl chloride was added, and the mixture was stirred at room temperature for 16 hours. The reaction mixture was partitioned between 1N hydrochloric acid and benzene. The organic layer was washed with water, and dried over anhydrous magnesium sulfate; and the solvent was evaporated to give 630 g of a yellow oil. By the following analytical data, this product was determined to be 1-acetoxy6-chloro-3,7-dimethyl-9-(2,6,6-trimethyl-1-cyclohexen-1-yl)-9-(p-tolyl)sulfonyl-2,7-nonadiene (18). It was found that from the NMR analysis, the oily product had a purity of 89%. Yield 88%.

NMR δ CDCl$_3$(CH$_3$)$_3$ SiOSi (CH$_3$)$_3$: 0.70–1.93 (m, 28H); 2.40 (s, 3H); 4.15–4.43 (m, 4H); 5.17 (t, 1H); 5.82 (d, 1H); 7.21 (d, 2H); 7.64 (d, 2H).

IR (film) ν (cm$^{-1}$): 1740 (C=O), 1150 (SO$_2$).

EXAMPLE 16

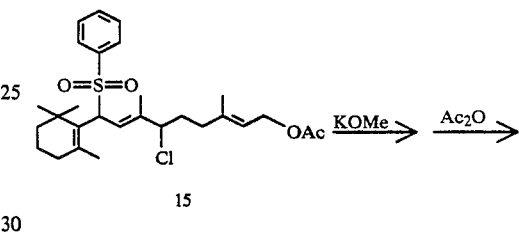

15

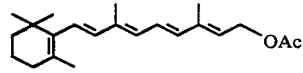

7

A 50 ml flask purged with argon gas was charged with 0.4951 g (0.977 mmole) of 1-acetoxy-6-chloro-3,7-dimethyl-9-(2,6,6-trimethyl-1-cyclohexen-1-yl)-9-phenylsulfonyl-2,7-nonadiene (15) and 15 ml of cyclohexane. After the mixture was stirred for a while, 0.70 g (10 mmoles) of potassium methoxide was added, and the mixture was stirred at 38° C. for 2 hours. To the reaction mixture were added 30 ml of diisopropyl ether and 15 ml of a saturated aqueous solution of ammonium chloride. The organic layer was separated, and the aqueous layer was extracted with 20 ml of diisopropyl ether. The extract was combined with the organic layer, and the mixture was washed with a saturated aqueous solution of ammonium chloride and dried over anhydrous magnesium sulfate. The organic solvent was evaporated from the organic layer, and the residue, together with 4 ml of a 0.05% by weight hexane solution of 2,6-di-t-butyl-4-methylphenol and 1.1 ml of triethylamine, was put in a 100 ml flask purged with argon. Under ice base cooling, 0.68 ml of acetic anhydride was added to the mixture, and the mixture was stirred for one day at room temperature. To the reaction mixture were added 50 ml of hexane and 10 ml of a saturated aqueous solution of sodium bicarbonate. The mixture was stirred for a while, and the hexane layer was separated. The hexane layer was washed with a saturated aqueous solution of sodium bicarbonate, and dried over anhydrous magnesium sulfate, By evaporating hexane from the hexane layer, 0.3462 g of a red oil was obtained. The FD-MASS analysis of this oily product revealed a peak at m/e=328. This led to the determination that the main component of the oily product was vitamin A acetate (7).

The vitamin A acetate was then quantified by high-performance liquid chromatography using methyl stearate as an internal standard. It was consequently found that the yield of vitamin A acetate was 70% based on 1-acetoxy-6-chloro-3,7-dimethyl-9-(2,6,6-trimethyl-1-cycloexen-1-yl)-9-phenylsulfonyl-2,7-nonadiene (15), and its all-trans content was 93%.

EXAMPLE 17

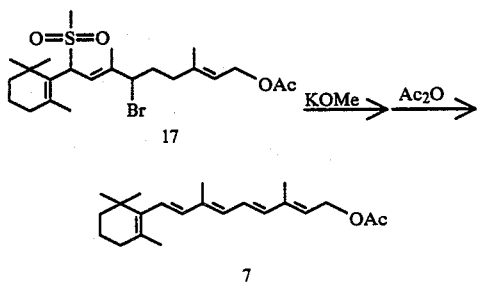

The same reaction and separating operations as in Example 16 were carried out except that 0.5538 g (1.01 mmoles) of 1-acetoxy-6-bromo-3,7-dimethyl-9-(2,6,6-trimethyl-1-cyclohexen-1-yl)-9-phenylsulfonyl-2,7-nonadiene 1-cyclohexen-1-yl)-9-phenylsulfonyl-2,7-nonadiene (17) obtained in Example 14 was used instead of 0.4951 g (0.977 mmole) of 1-acetoxy-6-chloro-3,7-dimethyl-9-(2,6,6-trimethyl-1-cyclphexen-1-yl)-9-phenylsulfonyl-2,7-nonadiene, and a mixture of 10 ml of cyclohexane and 5 ml of toluene was used instead of 15 ml of cyclohexane. As a result, 0.3195 g of a red oily product was obtained. The FD-MASS analysis of the oily product revealed a peak at m/e=328, and this led to the determination that the main component of the oily product was vitamin A acetate (7).

The resulting vitamin A acetate was quantified by high-performance liquid chromatography in the same way as in Example 16. It was found that the yield of vitamin A acetate was 70% based on 1-acetoxy-6-bromo-3,7-dimethyl-9-(2,6,6-trimethyl-1-cyclohexen-1-yl)-9-phenylsulfonyl-2,7-nonadiene (17), and its all-trans content was 93%.

EXAMPLE 18

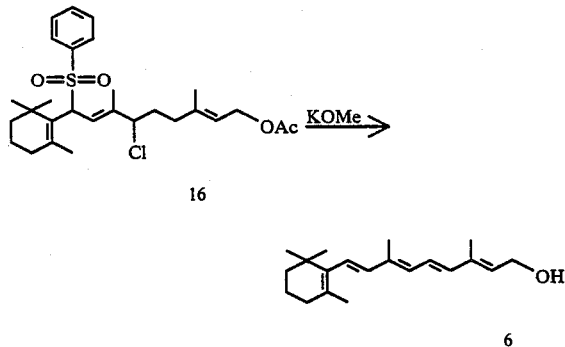

A 10 ml flask purged with argon gas was charged with 0.0232 g (0.050 mmole) of 6-chloro-1-hydroxy-3,7-dimethyl-9-(2,6,6-trimethyl-1-cyclohexen-1-yl)-9-phenylsulfonyl-2,7-nonadiene (16) obtained in Example 12, (B) and 5 ml of cyclohexane, and then 0.0352 g (0.50 mmole) of potassium methoxide was added. The mixture was stirred at 35° C. for 2 hours. The reaction mixture was added to a mixture of 20 ml of diisopropyl ether and 10 ml of a saturated aqueous solution of ammonium chloride. The organic layer was separated, dried over anhydrous magnesium sulfate, and concentrated to about 1 ml. The FD-MASS analysis of the concentrate revealed a peak at m/e=286. This led to the determination that the concentrate contained vitamin A (6).

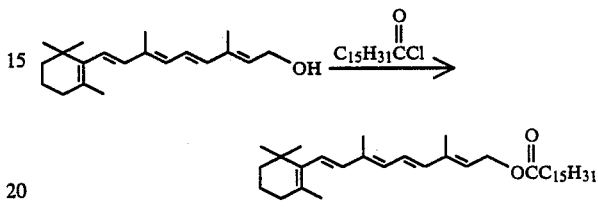

The above concentrate was dissolved in 2 ml of pyridine, and the solution was cooled with an ice water bath. Then, 0.0137 g (0.05 mmole) of palmitoyl chloride was added to the solution, and the mixture was stirred under ice bath cooling for 0.5 hour and then at room temperature for 5 hours. The reaction mixture was poured into a large amount of water, and extracted with hexane. The hexane extract was washed with water, and dried over anhydrous magnesium sulfate. The magnesium sulfate was removed by filtration, and hexane was evaporated from the filtrate under reduced pressure. As a result, 0.0282 g of a reddish yellow oil was obtained. The oil was determined, by liquid chromatography (column: μ-porasil; mobile phase: a 2:98 by volume mixture of diisopropyl ether and hexane), to contain 0.0183 g of vitamin A palmitate.

EXAMPLE 19

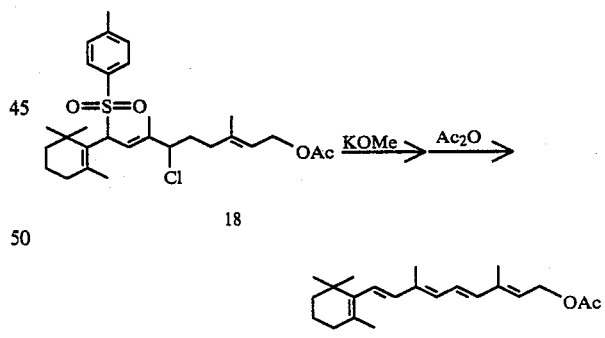

The same reaction and separating operations as in Example 17 were carried out except that 0.5127 g (0.985 mmole) of 1-acetoxy-6-chloro-3,7-dimethyl-9-(2,6,6-trimethyl-1-cyclohexen-1-yl)-9-(p-tolyl)sulfonyl-2,7-nonadiene (18) was used instead of 0.5538 g (1.01 mmoles) of 1-acetoxy-6-bromo-3,7-dimethyl-9-(2,6,6-trimethyl-1-cyclohexen-1-yl)-9-phenyl-sulfonyl-2,7-nonadiene. As a result, 0.3325 g of a red oily product was obtained. The FD-MASS analysis of the oily product revealed a peak at m/e=328. This led to the determination that the main component at the oily product was vitamin A acetate. Then, in the same way as in Example 16, the resulting vitamin A acetate was quantified by high-performance liquid chromatography. It was found that the yield of vitamin A acetate (7) was 68% based on 1-acetoxy-6-chloro-3,7-dimethyl-9-(2,6,6-trimethyl-1-cyclohexen-1-yl)-9-(p-tolyl)sulfonyl-2,7-nonadiene (18), and its all-trans content was 93%.

EXAMPLE 20

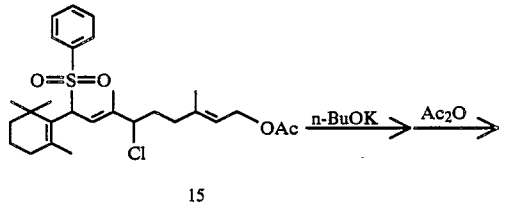

15

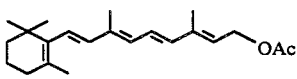

7

The same reaction and separating operations as in Example 16 were carried out except that 1.12 g (10 mmoles) of potassium n-butoxide was used instead of 0.70 g (10 mmoles) of potassium methoxide. As a result, 0.3481 g of a red oily product was obtained. In the same way as in Example 16, the resulting vitamin A acetate was quantified by high-performance liquid chromatography. It was found that the yield of vitamin A acetate (7) was 72% based on 1-acetoxy-6-chloro-3,7-dimethyl-9-(2,6,6-trimethyl-1-cyclohexen-1-yl)-9-phenylsulfonyl-2,7-nonadiene (15), and its all-trans content was 92%.

EXAMPLE 21

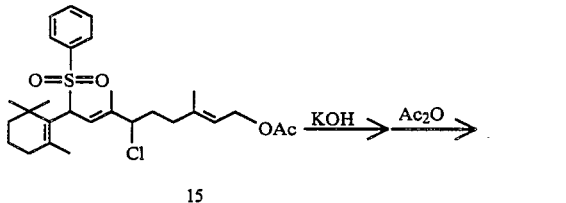

15

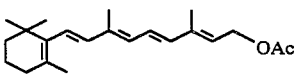

7

A 50 ml flask purged with argon gas was charged with 0.4913 g (0.970 mmole) of 1-acetoxy-6-chloro-3,7-dimethyl-9-(2,6,6-trimethyl-1-cyclohexen-1-yl)-9-phenylsulfonyl-2,7-nonadiene (15) obtained in Example 12, (A) and 15 ml of cyclohexane. The mixture was stirred for a while, and 0.55 g (10 mmoles) of potassium hydroxide (purity 85%) was added. The mixture was stirred at 65° C. for 1.5 hours, and further at the refluxing temperature for 2 hours. After cooling, 30 ml of diisopropyl ether and 15 mml of a saturated aqueous solution of ammonium chloride were added to the reaction mixture. The organic layer was separated, and the aqueous layer was extracted with 20 ml of diisopropyl ether. The extract was combined with the organic layer, and the mixture was washed with a saturated aqueous solution of ammonium chloride, and dried over anhydrous magnesium sulfate. The organic solvent was evaporated from the organic layer, and the residue, together with 5 ml of a 0.05% by weight hexane solution of 2,6-di-t-butyl-4-methylphenol and 1.1 ml of triethylamine, was put in a 100 ml flask purged with argon. Under ice bath cooling, 0.68 ml of acetic anhydride was added to the mixture. The mixture was stirred at room temperature for 1 day. To the reaction mixture were added 50 ml of hexane and 10 l of a saturated aqueous solution of sodium bicarbonate. The mixture was stirred for a while, and the hexane layer was separated. The hexane layer was washed with a saturated aqueous solution of sodium bicarbonate, and dried over anhydrous magnesium sulfate. Hexane was evaporated from the hexane solution to give 0.3577 g of a red oily product. The resulting vitamin A acetate was quantified by high-performance liquid chromatography in the same way as in Example 16. It was found that the yield of vitamin A acetate (7) was 64% based on 1-acetoxy-6-chloro-3,7-dimethyl-9-(2,6,6-trimethyl-1-cyclohexen-1-yl)-9-phenylsulfonyl-2,7-nonadiene, and its all-trans content was 90%.

EXAMPLE 22

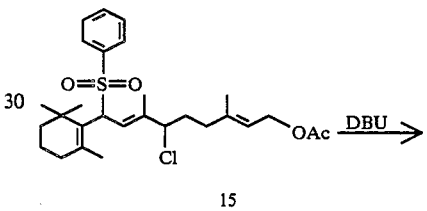

15

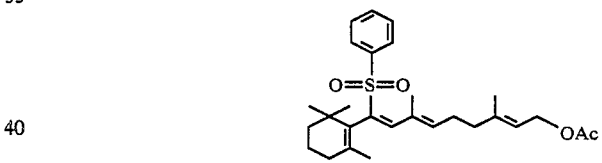

19

A 50 ml flask was charged with 1.55 g (3.1 mmoles) of 1-acetoxy-6-chloro-3,7-dimethyl-9-(2,6,6-trimethyl-1-cyclohexen-1-yl)-9-phenylsulfonyl-2,7-nonadiene (15) obtained in Example 12, (A), 30 ml of diethyl ether and 0.85 ml (6.0 mmoles) of 1,8-diazabicyclo[5.4.0]undec-7-ene, and the mixture was stirred for 10 hours under reflux. The reaction mixture was partitioned between diethyl ether and water. The ether layer was washed successively with 5% sulfuric acid and a saturated aqueous solution of sodium bicarbonate, and dried over anhydrous magnesium sulfate. The solvent was evaporated from the ether solution, and the residue was chromatographed on a silica gel column using an eluent composed of a 3:1 by volume mixture of hexane and ethyl acetate to give 1.23 g of a yellow oily product. By the following analytical data, this product was determined to be 1-acetoxy-3,7-dimethyl-9-(2,6,6-trimethyl-1-cyclohexen-1-yl)-9-phenylsulfonyl-2,6,8-nonatriene (19). Yield 86%.

NMR δ CDCl$_3$(CH$_3$)$_3$SiOSi(CH$_3$)$_3$: 0.86–2.27 (m, 28H); 4.51 (d, 2H); 5.25 (t, 1H); 5.67–5.90 (m, 1H); 7.14–7.90 (m, 6H).

IR (film) ν (cm$^{-1}$): 1745 (C=O), 1150 (SO$_2$).

FD-MASS m/e: 470 (M$^+$), 328 (M$^+$—C$_6$H$_5$SO$_2$).

EXAMPLE 23

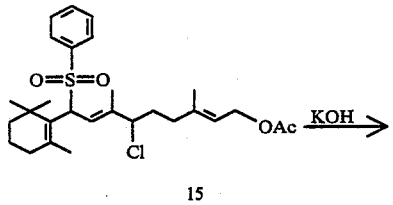

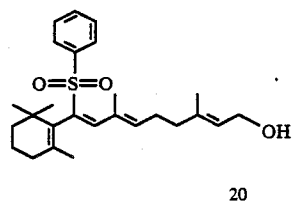

A 100 ml flask was charged with 2.5347 g (5.00 mmoles) of 1-acetoxy-6-chloro-3,7-dimethyl-9-(2,6,6-trimethyl-1-cyclohexen-1-yl)-9-phenylsulfonyl-2,7-nonadiene (15) obtained in Example 12, (A), 6 ml of benzene and 20 ml of methanol, and the mixture was stirred to form a solution. The solution was cooled with an ice water bath, and a solution of 1.35 g (20 mmoles) of potassium hydroxide (purity 85%) in 15 ml of methanol was added. The mixture was stirred in an ice water bath for 5 minutes, and further at room temperature for 18 hours. A saturated aqueous solution of ammonium chloride was added to the reaction mixture, and the mixture was extracted successively with three 100 ml portions of diethyl ether. The extracts were washed with a saturated aqueous solution of ammonium chloride and dried over anhydrous magnesium sulfate. The solvent was evaporated from the ether solution, and the residue was chromatographed on a silica gel column using an eluent composed of a mixture of hexane and ethyl acetate in a volume ratio of from 4:1 to 3:1 to give 1.5071 g of a yellow oily product. By the following analytical data, the product was determined to be 1-hydroxy-3,7-dimethyl-9-(2,6,6-trimethyl-1-cyclohexen-1-yl)-9-phenylsulfonyl-2,6,8nonatriene (20). Yield 70%.

NMR δ CDCl$_3$(CH$_3$)$_3$SiOSi(CH$_3$)$_3$): 0.90–2.28 (m, 26H); 4.07 (m, 2H); 5.35 (t, 1H0; 5.67–5.89 (m, 1H); 7.13–7.90 (m, 6H).

IR (film) ν (cm$^{-1}$): 3450 (OH), 1140 (SO$_2$).

FD-MASS m/e: 428 (M$_+$), 287 (M$^+$—C$_6$H$_5$SO$_2$).

EXAMPLE 24

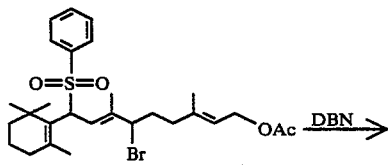

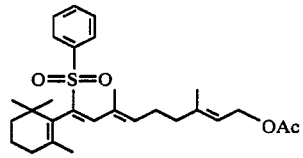

A 50 ml flask was charged with 1.38 g (2.5 mmoles) of 1-acetoxy-6-bromo-3,7-dimethyl-9-(2,6,6-trimethyl-1-cyclohexen-1-yl)-9-phenylsulfonyl-2,7-nonadiene (17) obtained in Example 14, 15 ml of methylene chloride, and 0.6 ml (5 mmoles) of 1,5-diazabicyclo[4.3.0]non-5-ene. The mixture was stirred for 5 hours under reflux. The reaction mixture was worked up by the same operation as in Example 22, to give 0.99 g (yield 84%) of 1-acetoxy-3,7-dimethyl- 9-(2,6,6-trimethyl-1-cyclohexen-1-yl)-9-phenylsulfonyl-2,6,8-nonatriene (19).

EXAMPLE 25

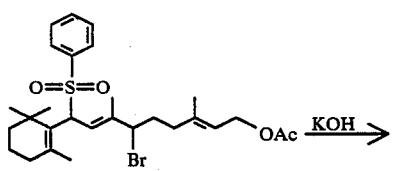

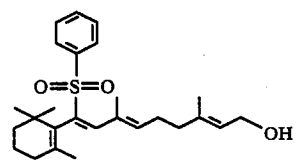

The same reaction and separating operations as in Example 23 were carried out except that 1.36 g (2.6 mmoles) of 1-acetoxy-6-bromo-3,7-dimethyl-9-(2,6,6-trimethyl-1-cyclohexen-1-yl)-9-phenylsulfonyl-2,7-nonadiene (17) obtained in Example 14 was used instead of 2.5347 g (5.00 mmoles) of 1-acetoxy-6-chloro-3,7-dimethyl-9-(2,6,6-trimethyl-1-cyclohexen-1-yl)-9-phenylsulfonyl-2,7-nonadiene (15). As a result, 0.87 g (yield 73%) of 1-hydroxy-3,7-dimethyl-9-(2,6,6-trimethyl-1-cyclohexen-1-yl)-9-phenylsulfonyl-2,6,8-nonatriene was obtained.

EXAMPLE 26

(A)

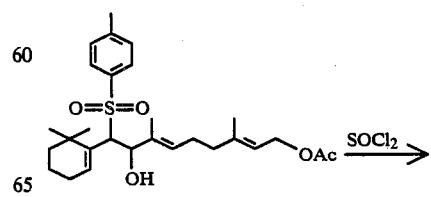

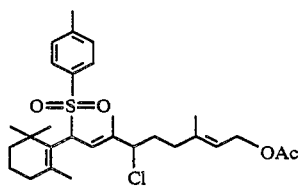

A 100 ml flask was charged with 4.27 g (8.82 mmoles) of 1-acetoxy-8-hydroxy-3,7-dimethyl-9-(2,6,6-trimethyl-1-cyclohexen-1-yl)-9-(p-tolyl)sulfonyl-2,6-nonadiene (10) obtained in Example 4, (A), 6.7 ml (84 mmoles) of pyridine and 50 ml of benzene. While the flask was cooled with an ice water bath, 0.77 ml (11 mmoles) of thionyl chloride was added, and the mixture was then stirred at room temperature for 16 hours. The reaction mixture was partitioned between 1N hydrochloric acid and benzene. The organic layer was washed with water, and dried over anhydrous magnesium sulfate. The solvent was evaporated to give 4.41 g of a yellow oily product. By the following analytical data, this product was determined to the 1-acetoxy-6-chloro-3,7-dimethyl-9-(2,6,6-trimethyl-1-cyclohexen-1-yl)-9-(p-tolyl)sulfonyl-2,7-nonadiene (18). From the NMR analysis, the purity of the oily product was found to be 89%. Yield 88%.

NMR δ CDCl₃(CH₃)₃SiOSi(CH₃)₃: 0.70–1.93 (m, 28H); 2.40 (s, 3H); 4.15–4.43 (m, 4H); 5.17 (t, 1H); 5.82 (d, 1H); 7.21 (d, 2H); 7.64 (d, 2H).

IR (film) ν (cm⁻¹): 1740 (C=O), 1150 (SO₂).

(B-1)

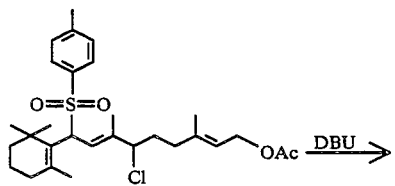

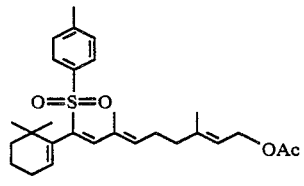

The same reaction and separating operations as in Example 22 were carried out except that 1.75 g (3.0 mmoles) of 1-acetoxy-6-chloro-3,7-dimethyl-9-(2,6,6-trimethyl-1-cyclohexen-1-yl)-9-(p-tolyl)sulfonyl-2,7-nonadiene (18) (purity 89%) was used instead of 1.55 g (3.1 mmoles) of 1-acetoxy-6-chloro-3,7-dimethyl-9-(2,6,6-trimethyl-1-cyclohexen-1-yl)-9-phenylsulfonyl-2,7-nonadiene (15). As a result, 1.19 g of a yellow oily product was obtained. By the following analytical data, this product was determined to be 1-acetoxy-3,7-dimethyl-9-(2,6,6-trimethyl-1-cyclohexen-1-yl)-9-(p-tolyl)sulfonyl2-6,8-nonatriene (21). Yield 82%.

NMR δ CDCl₃(CH₃)₃SiOSi(CH₃)₃: 0.87–2.25 (m, 28H); 2.40 (s, 3H0; 4.51 (d, 2H); 5.24 (t, 1H); 5.66–5.90 (m, 1H); 7.14–7.98 (m, 5H).

IR (film) ν (cm⁻¹): 1745 (C=O), 1150 (SO₂).

FD-MASS m/e: 484 (M⁺), 328 (M⁺—CH₃C₆H₄SO₂H).

(B-2)

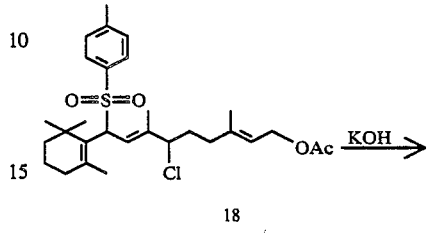

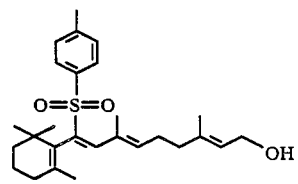

The same reaction and separating operations as in Example 23 were carried except that 2.92 g (5.0 mmoles) of 1-acetoxy-6-chloro-3,7-dimethyl-9-(2,6,6-trimethyl-1-cyclohexen-1-1yl)-9-(p-tolyl)sulfonyl-2,7-nonadiene (18) (purity 89%) was used instead of 2.5347 g (5.00 mmoles) of 1-acetoxy-6-chloro-3,7-dimethyl-9-(2,6,6-trimethyl-1-cyclohexen-1-yl) 9-phenylsulfonyl-2,7-nonadiene (15). As a result, 1.45 g of a yellow oil was obtained. By the following analytical data, the oil was determined to be 1-hydroxy-3,7-dimethyl9-(2,6,6-trimethyl-1-cyclohexen-1-yl)-9-(p-tolyl)sulfonyl2,6,8-nontriene (22). Yield 66%.

NMR δ CDCl₃(CH₃)₃SiOSi(CH₃)₃:
0.89–2.27 (m, 26H); 2.40 (s, 3H); 4.06 (m, 2H); 5.33 (t, 1H); 5.67–5.89 (m, 1H); 7.13–7.99 (m, 5H).

IR (film) ν (cm⁻¹): 3450 (OH), 1140 (SO₂).

FD-MASS m/e: 442 (M⁺), 287 (M⁺—CH₃C₆H₄SO₂).

EXAMPLE 27

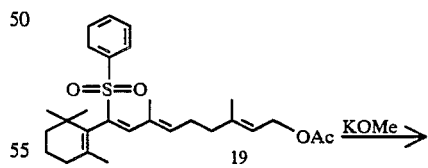

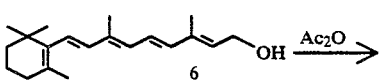

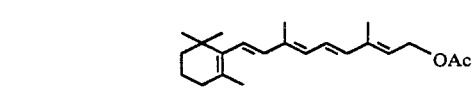

A 50 ml flask purged with argon gas was charged with 0.4812 g (1.02 mmoles) of 1-acetoxy-3,7-dimethyl- 9-(2,6,6-trimethyl-1-cyclohexen-1-yl)-9-phenylsulfonyl2,6,8-nonatriene (19), 15 ml of cyclohexane and 0.70 g (10 mmoles) of potassium methoxide, and the mixture was stirred at 38° C. for 2 hours. The reaction mixture was partitioned between 30 ml of diisopropyl ether and 15 ml of a saturated aqueous solution of ammonium chloride. The aqueous layer was extracted with 20 ml of diisopropyl ether, and the extract was combined with the organic layer. The mixture was washed with a saturated aqueous solution of ammonium chloride, and dried over anhydrous magnesium sulfate. The solvent was removed from the organic layer, and the residue, together with 4 ml of a 0.05% by weight hexane solution of 2,6-di-t-butyl-4-methylphenol and 1.1 ml of triethylamine, was put in a 100 ml flask purged with argon gas. To the mixture was added 0.68 ml of acetic anhydride, and the entire mixture was stirred at room temperature for one day. The reaction mixture was stirred for a while together with 50 ml of hexane and 10 ml of a saturated aqueous solution of sodium bicarbonate, and the hexane layer was separated. The hexane layer was washed with a saturated aqueous solution of sodium bicarbonate, and dried over anhydrous magnesium sulfate. Hexane was evaporated from the hexane solution to give 0.3276 g of a red oily product. The FD-MASS analysis of the oily product revealed a peak at m/e=328. This led to the determination that the main component of the oily product was vitamin A acetate (7). The resulting vitamin A acetate was quantified by high-performance liquid chromatography using methyl stearate as an internal standard. It was found that the yield of vitamin A acetate was 74% based on 1-acetoxy-3,7-dimethyl-9-(2,6,6-trimethyl-1-cyclohexen-1-yl)-9-phenylsulfonyl-2,6,8-nonatriene (19), and its all-trans content was 93%.

EXAMPLE 28

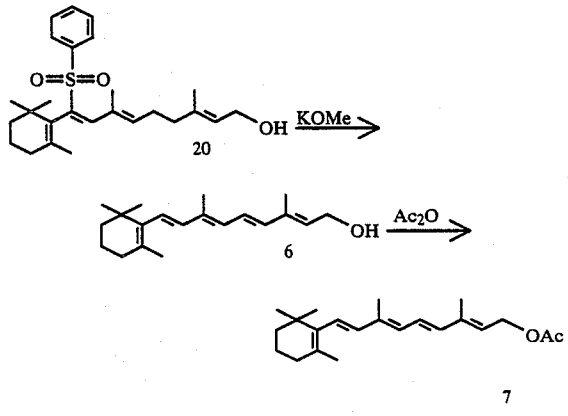

The same reaction and separating operations as in Example 27 were carried out except that 0.4495 g (1.05 mmoles) of 1-hydroxy-3,7-dimethyl-9-(2,6,6-trimethyl-1cyclohexen-1-yl)-9-phenylsulfonyl-2,6,8-nonatriene (20) obtained in Example 23 was used instead of 0.4812 g (1.02 mmoles) of 1-acetoxy-3,7-dimethyl-9-(2,6,6-trimethyl-1cyclohexen-1-yl)-9-phenylsulfonyl-2,6,8-nonatriene (19). As a result, 0.3285 g of a red oily product was obtained. In the same way as in Example 27, the resulting vitamin A acetate (7) was quantified by high-performance liquid chromatography. It was found that the yield of vitamin A acetate was 77% based on 1-hydroxy-3,7-dimethyl-9-(2,6,6trimethyl-1-cyclohexen-1-yl)-9-phenylsulfonyl-2,6-8-nonatriene (20), and its all-trans content was 93%.

EXAMPLE 29

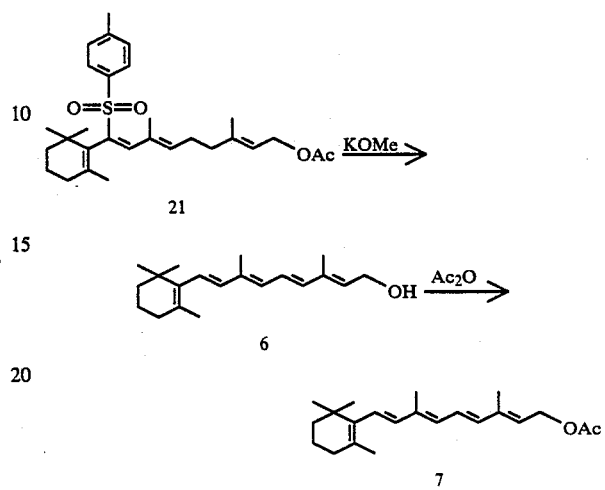

The same reaction and separating operations as in Example 27 were carries out except that 0.5227 g (1.08 mmoles) of 1-acetoxy-3,7-dimethyl-9-(2,6,6-trimethyl-1-cyclohexen-1-yl)-9-(p-tolyl)sulfonyl-2,6,8-nonatriene (21) obtained in Example 26, (B-1) was used instead of 0.4812 g (1.02 mmoles) of 1-acetoxy-3,7-dimethyl-9-(2,6,6-trimethyl1-cyclohexen-1-yl)-9-phenylsulfonyl-2,6,8-nonatriene (19). As a result, 0.3156 g of a red oily product was obtained. The resulting vitamin A acetate (7) was quantified by high-performance liquid chromatography in the same way as in Example 27. It was found that the yield of vitamin A acetate was 70% based on 1-acetoxy-3,7-dimethyl-9-(2,6,6-trimethyl-1-cyclohexen-1-yl)-9-(p-tolyl)sulfonyl-2,6,8-nonatriene (21), and its all-trans content was 93%.

EXAMPLE 30

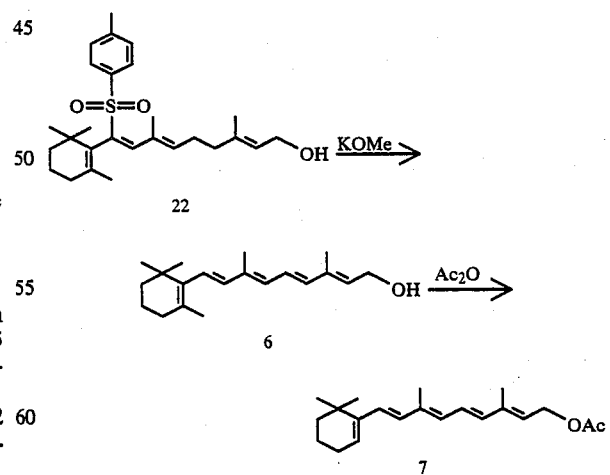

The same reaction and separating operations as in Example 27 were carried out except that 0.4464 g (1.01 mmoles) of 1-hydroxy-3,7-dimethyl-9-(2,6,6-trimethyl-1cyclohexen-1-yl)-9-(p-tolyl)sulfonyl-2,6,8-nonatriene (22) obtained in Example 26, (B-1) was used instead of 0.4812 g (1.02 mmoles) of 1-acetoxy-3,7-dimethyl-9-(2,6,6-trimethyl-1-cyclohexen-1-yl)-9-phenylsulfonyl-2,6,8-nonatriene (19). As a result, 0.3201 g of a red oily product was obtained. In the same way as in Example 27, the resulting vitamin A acetate (7) was quantified by high-performance liquid chromatography. It was found that the yield of vitamin A acetate was 74% based on 1-hydroxy-3,7-dimethyl-9-(2,6,6-trimethyl-1-cyclohexen-1-yl)-9-(p-tolyl)-sulfonyl-2,6,8-nonatriene (22), and its all-trans content was 93%.

EXAMPLE 31

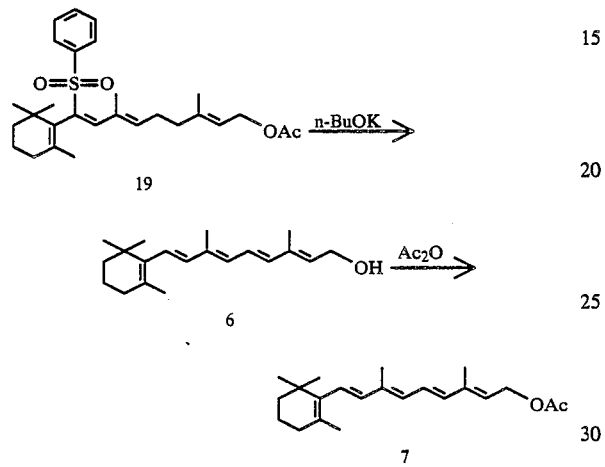

The same reaction and separating operations as in Example 27 were carried out except that 1.12 g (10 mmoles) of potassium n-butoxide was used instead of 0.70 g (10 mmoles) of potassium methoxide. As a result, 0.3481 g of a red oily product was obtained. In the same way as in Example 27, the resulting vitamin A acetate (7) was quantified by high-performance liquid chromatography. It was found that the yield of vitamin A acetate was 72% based on 1-acetoxy-3,7-dimethyl-9-(2,6,6-trimethyl-1-cyclohexen-1-yl)-9-phenylsulfonyl-2,6,8-nonatriene (19), and its all trans content was 92%.

EXAMPLE 32

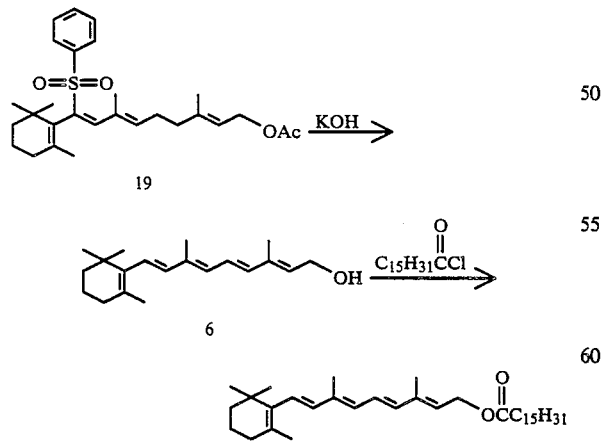

A 10 ml flask purged with argon gas was charged with 0.0235 g (0.050 mmole) of 1-acetoxy-3,7-dimethyl-9-(2,6,6-trimethyl-1-cyclohexen-1-yl)-9-phenylsulfonyl-2,6,8-nonatriene (19) obtained in Example 22 and 6 ml of cyclohexane, and then 0.07 g (1 mmole) of potassium hydroxide (purity 85 %) was added. The mixture was stirred for 2 hours at the refluxing temperature. The reaction mixture was added to a mixture of 20 ml of diisopropyl ether and 10 ml of a saturated aqueous solution of ammonium chloride. The organic layer was separated, dried over anhydrous magnesium sulfate, and concentrated to about 1 ml. The FD-MASS analysis of the concentrate revealed a peak at m/e=286. This led to the determination that the concentrate contained vitamin A (6).

The concentrate was dissolved in 2 ml of pyridine, and cooled in an ice bath. Palmitoyl chloride (0.0137 g; 0.05 mmole) was added to the solution, and the mixture was stirred under ice bath cooling for 0.5 hour, and further at room temperature for 5 hours. The reaction mixture was poured into a large amount of water, and extracted with hexane. The hexane extract was washed with water, and then dried over anhydrous magnesium sulfate. The magnesium sulfate was separated by filtration, and hexane was evaporated from the filtrate under reduced pressure. As a result, 0.0282 g of a reddish yellow oil was obtained. The oil was determined to contain 0.0183 g of vitamin A palmitate from the results of analysis by liquid chromatography (column: μ-porasil; mobile phase: a 2:98 by volume mixture of diisopropyl ether and hexane).

EXAMPLE 33

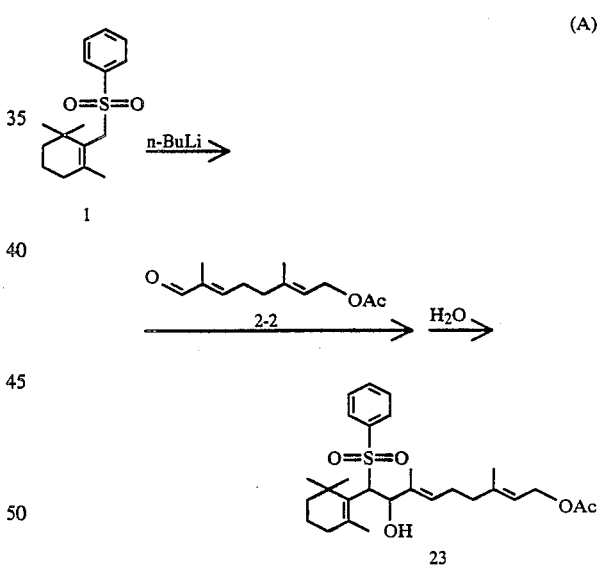

A 200 ml flask purged with argon gas was charged with 8.70 g (31.2 mmoles) of beta-cyclogeranyl phenyl sulfone and 60 ml of tetrahydrofuran, and cooled to -78° C. Then, 20.8 ml (31.2 mmoles) of a hexane solution of n-butyllithium (1.5 moles/liter) was added dropwise, and the mixture was stirred at the above temperature for 3 hours. Then, a solution of 6.59 g (31.3 mmoles) of 8-acetoxy-2,6-dimethyl-2(E),6(Z)-octadien-1-al in 15 ml of tetrahydrofuran was added dropwise at −78° C., and the mixture was stirred at this temperature for 2 hours. The mixture was further stirred at −50° C. for 2 hours. The reaction mixture was cooled to −78° C., and water was added. The temperature of the mixture was raised to room temperature. The resulting mixture was extracted with three 100 ml portions of benzene. The extracts were washed with water, and dried over anhydrous sodium sulfate. Benzene was evaporated from the extract, and the residue was chromatographed on a silica gel column using an eluent composed of a mixture of hexane and ethyl acetate in a volume ratio of 5:1 to give 13.87 g of a colorless transparent oil. By the following analytical data, this product was determined to be 1-acetoxy-8-hydroxy-3,7-dimethyl-9-(2,6,6-trimethyl-1-cyclohexen-1-yl)-9-phenylsulfonyl-2(Z),6(E)-nonadiene (23).

Yield 91%.

NMR δ CDCl$_3$(CH$_3$)$_3$SiOSi(CH$_3$)$_3$: 0.60–2.20 (m, 28H); 3.67 (br, 1H); 3.98 (d, 1H); 4.50 (d, 2H); 5.00 (d, 1H); 5.34 (m, 2H); 7.66–8.20 (m, 5H).

IR (film) (cm$^{-1}$): 3500 (OH), 1735 (C=O), 1140 (SO$_2$).

FD-MASS m/e: 488 (M+).

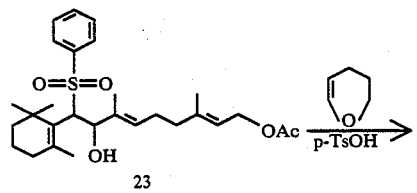

23

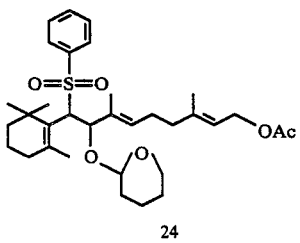

24

A 100 ml flask was charged with 4.88 g (10 mmoles) of compound (23), 0.02 g (0.1 mmole) of p-toluenesulfonic acid monohydrate and 30 ml of methylene chloride, and cooled with an ice water bath. 2.6 ml (30 mmoles) of 3,4-dihydro-2H-pyran was added dropwise. After the addition, the mixture was stirred at the above temperature for 2 hours.

Sodium bicarbonate (0.52 g) was added to the reaction mixture. The mixture was stirred for 5 minutes, and then 20 ml of a saturated aqueous solution of sodium bicarbonate was added. The resulting mixture was extracted with 100 ml of diethyl ether. The extract was washed with 20 ml of a saturated aqueous solution of sodium bicarbonate, and dried over anhydrous magnetism sulfate. The solvent was evaporated by an evaporator, and the residue was chromatographed on a silica gel column using an eluent composed of a 1:5 mixture of ethyl acetate and n-hexane to give 5.75 g of compound (24). Yield 100%. The analytical data of the product were as follows:

NMR δ CDCl$_3$(CH$_3$)$_3$SiOSi(CH$_3$)$_3$: 0.60–2.02 (m, 34H); 3.17–5.40 (m, 9H); 7.38–8.11 (m, 5H).

IR (film) ν (cm$^{-1}$): 1745 (C=O), 1150 (SO$_2$)

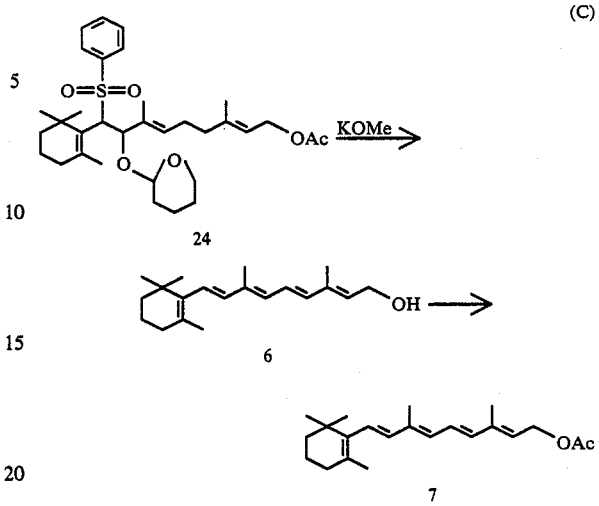

Under an argon gas atmosphere, a 50 ml flask was charged with 0.5678 g (0.993 mmole) of compound (24), 15 ml of cyclohexane and 0.70 g (10 mmoles) of potassium methoxide, and the mixture was stirred for 1.5 hours at 40° C.

The reaction mixture was poured into a mixture of 50 ml of diisopropyl ether and 15 ml of a saturated aqueous solution of ammonium chloride, and the organic layer was separated. The organic layer was washed with 10 ml of a saturated aqueous solution of ammonium chloride, and dried over anhydrous magnesium sulfate. The solvent was evaporated by an evaporator. The residue was dissolved in 4 ml of hexane and transferred to a 50 ml brown flask.

The flask was cooled in an ice water bath, and 1.1 ml of triethylamine and 0.68 ml of acetic anhydride were added. The mixture was stirred for one day at room temperature.

The reaction mixture was poured into a mixture composed of 50 ml of hexane and 10 ml of saturated aqueous solution of sodium bicarbonate, and the organic layer was separated. The organic layer was washed twice with 10 ml of a saturated aqueous solution of sodium bicarbonate, and dried over anhydrous magnesium sulfate. The solvent was evaporated by an evaporator to give 0.3535 g of an orange-colored oily product. By high-performance liquid chromatography (column: μ-porasil; mobile phase: a 9:1 mixture of hexane and diisopropyl ether), this oily product was found to contain 0.248 g of vitamin A acetate (7). Yield 76%. The content of the 13-cis isomer in the vitamin A acetate was 90%.

What is claimed is:

1. A process for producing vitamin A represented by the formula

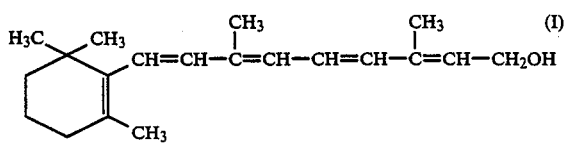

which comprises treating a compound represented by the formula

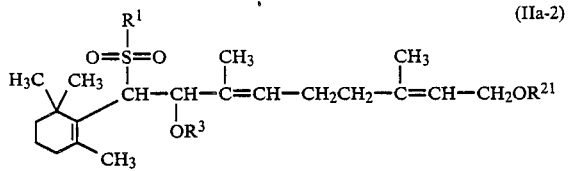

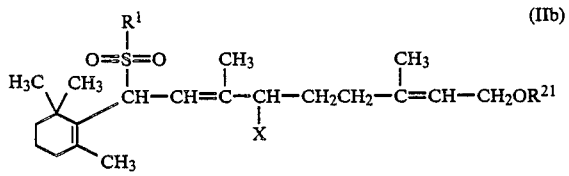

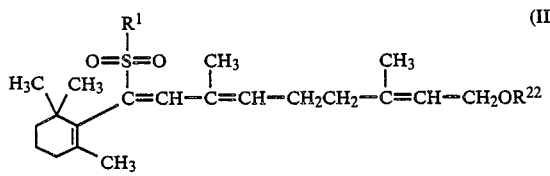

wherein R¹ represents an aryl group which may be substituted, R²¹ and R²² each represent a hydrogen atom or a lower alkanoyl group, R³ represents an acetal-type protective group for a hydroxyl group, and X represents a halogen atom, with a base, selected from the group consisting of lower alkoxides of potassium and potassium hydroxide, in a solvent selected from the group consisting of aliphatic hydrocarbons and aromatic hydrocarbons, thereby producing vitamin A substantially maintaining the sterochemistry of the starting compound.

2. The process of claim 1, wherein the base is selected from the group consisting of potassium methoxide and potassium n-butoxide.

3. The process of claim 2 wherein the base is potassium methoxide.

4. The process of claim 1 wherein the treatment is carried out at a temperature of 20° to 80° C.

5. The process of claim 1 wherein the treatment is carried out in an atmosphere of an inert gas.

6. The process of claim 1 wherein the solvent is selected from the group consisting of toluene, cyclohexane and a mixture of toluene and cyclohexane.

7. The process of claim 2 wherein the solvent is selected from the group consisting of toluene, cyclohexane and a mixture of toluene and cyclohexane.

8. The process of claim 3 wherein the solvent is selected from the group consisting of toluene, cyclohexane and a mixture of toluene and cyclohexane.

* * * * *